(12) United States Patent
Takeshita

(10) Patent No.: US 9,708,577 B2
(45) Date of Patent: Jul. 18, 2017

(54) APPARATUS FOR CONTROLLING AMMONIA AND A METHOD FOR CONTROLLING AMMONIA

(71) Applicant: Ajinomoto Co., Inc., Chuo-ku, Tokyo (JP)

(72) Inventor: Ryo Takeshita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 14/815,328

(22) Filed: Jul. 31, 2015

(65) Prior Publication Data

US 2015/0337254 A1 Nov. 26, 2015

Related U.S. Application Data

(63) Continuation of application No. PCT/JP2014/076468, filed on Oct. 2, 2014.

(30) Foreign Application Priority Data

Oct. 2, 2013 (JP) ................................. 2013-207519

(51) Int. Cl.
| | | |
|---|---|---|
| *C12M 1/34* | (2006.01) |
| *C12P 13/08* | (2006.01) |
| *C12P 13/10* | (2006.01) |
| *C12M 1/36* | (2006.01) |
| *C12N 1/20* | (2006.01) |
| *C12P 13/24* | (2006.01) |

(52) U.S. Cl.
CPC ............ *C12M 41/34* (2013.01); *C12M 41/26* (2013.01); *C12M 41/32* (2013.01); *C12M 41/48* (2013.01); *C12N 1/20* (2013.01); *C12P 13/08* (2013.01); *C12P 13/10* (2013.01); *C12P 13/24* (2013.01)

(58) Field of Classification Search
None
See application file for complete search history.

(56) References Cited

U.S. PATENT DOCUMENTS

| 6,391,262 B1 | 5/2002 | Brinton et al. |
| 2007/0243590 A1 | 10/2007 | Takeshita et al. |
| 2012/0077258 A1 | 3/2012 | Foertsch et al. |

FOREIGN PATENT DOCUMENTS

| DE | 102011016604 A1 | 10/2012 |
| JP | 63-024149 A | 2/1988 |
| JP | 63-115048 A | 5/1988 |
| JP | 05-177196 A | 7/1993 |
| JP | 08-262005 A | 10/1996 |
| JP | 11-174011 A | 7/1999 |
| JP | 2007-244341 A | 9/2007 |
| JP | 2012-518161 A | 8/2012 |
| RU | 2268299 C2 | 9/2005 |
| RU | 2350655 C2 | 11/2008 |
| WO | WO 00/18947 A1 | 4/2000 |
| WO | WO 2006/038695 A1 | 4/2006 |
| WO | WO 2012/139563 A1 | 10/2012 |

OTHER PUBLICATIONS

English Translation for JP 11-174011 of Tanaka, Published in 1999, 19 pgs.*
Kole et al. "Ammonium Concentration Control in Fed-Batch Fermentations for the Production of Biomass and Enzymes" From the Book: Biotechnology Research and Applications pp. 94-103, Copyright 1988, Publisher Springer Netherlands.*
Thermo Scientific "User Guide: Standard Ammonia Ion Selective Electrode" Document 258743-001 Rev. A 02-09, publised 2009, 47 pgs.*

* cited by examiner

*Primary Examiner* — Thane Underdahl
(74) *Attorney, Agent, or Firm* — Foley & Lardner LLP

(57) ABSTRACT

An method for controlling ammonia concentration of a culture medium contained in a culture tank, by using an ammonia-controlling apparatus comprising at least an ammonia feeder that supplies ammonia to the culture tank, an ammonia sensor that responds to non-ionized ammonia in the culture medium contained in the culture tank, and a control part connected to the ammonia feeder and the ammonia sensor, and which method comprises the following steps performed by the control part: calculating non-ionized ammonia concentration of the culture medium contained in the culture tank from the signal from the ammonia sensor by using a calibration curve representing relation between non-ionized ammonia concentration of the culture medium contained in the culture tank and a signal from the ammonia sensor; and directing the ammonia feeder to supply ammonia to the culture tank when the calculated non-ionized ammonia concentration is lower than a predetermined concentration.

13 Claims, 9 Drawing Sheets

FIG. 1A

Input of signal from ammonia sensor responding to non-ionized ammonia in culture medium in culture tank

↓

Ammonia-controlling apparatus performs the following steps:

Calibration curve creation step

Non-ionized ammonia concentration calculation step

Ammonia supply direction step

↓

Output of direction to ammonia feeder supplying ammonia to culture tank

FIG. 1B

Input of signal from ammonia sensor responding to non-ionized ammonia in culture medium in culture tank Input of measured pH of culture medium in culture tank

↓ ↓

Ammonia-controlling apparatus performs the following steps:

Calibration curve creation step

Non-ionized ammonia concentration calculation step

Total ammonia concentration calculation step

Ammonia supply direction step

↓

Output of direction to ammonia feeder supplying ammonia to culture tank

APPARATUS FOR CONTROLLING AMMONIA AND A METHOD FOR CONTROLLING AMMONIA

CROSS-REFERENCE TO RELATED APPLICATIONS

This application is a continuation of International Patent Application No. PCT/JP2014/076468 filed Oct. 2, 2014, which claims the benefit of Japanese Patent Application No. 2013-207519 filed Oct. 2, 2013, the contents of which are incorporated herein by reference in their entireties.

TECHNICAL FIELD

The present invention relates to an apparatus for controlling ammonia and a method for controlling ammonia, especially an apparatus and a method for controlling ammonia concentration of a culture medium contained in a culture tank.

BACKGROUND

Ammonia is an important supply source of nitrogen and an indispensable nutrient used for fermentation.

An existing technique for measuring ammonia concentration involves a technique of using an ion electrode.

For example, in the method described in WO2006/038695, the ammonia concentration in a liquid fermentation medium is controlled to be below a certain concentration, and thereby fermentation bacteria are cultured at a higher pH value. The counter ions to be added to the medium for the production of a basic substance by fermentation are thereby reduced, and the manufacturing process is significantly simplified as a result.

However, the above-mentioned conventional technique has a problem that it is difficult to directly control the ammonia concentration in the liquid fermentation medium, that is, directly measure or control the ammonia concentration in a culture medium contained in a culture tank during the culture, by that technique.

Namely, it has a problem that, as shown in FIG. 9 (flowchart showing an example of the conventional process of ammonia concentration control), in order to know the total ammonia concentration (total concentration of $NH_3$ and $NH_4^+$) in the culture medium, the conventional process requires a series of operations of sampling the culture medium from the inside of the culture tank (Step SA-1), mixing the sampled culture medium with a strongly alkaline reaction mixture (for example, NaOH) (Step SA-2), and continuously measuring the existing ammonia converted into non-ionized ammonia ($NH_3$) out of the culture tank (Step SA-3). That is, it is difficult to sterilely perform the series of operations for the measurement with the sampled culture medium out of the culture tank. Moreover, since the culture medium used for the measurement contains the strongly alkaline reaction mixture (for example, NaOH), it cannot be recycled into the culture tank and must be discarded. Therefore, a higher measurement frequency invites larger waste of the culture medium, and the number of times of actual measurement is limited (Step SA-4).

Furthermore, in the culture tank, ammonia is continuously consumed, but the ammonia consumption rate is not constant. Therefore, it also has a problem that, as shown in FIG. 9, even if the ammonia concentration is measured by the above-mentioned sampling operation with a certain interval (Step SA-5), the short period trend thereof is not known, and therefore the ammonia concentration in the culture medium cannot be controlled to be constant (Step SA-6).

Furthermore, even if the non-ionized ammonia ($NH_3$) partly existing in the culture medium is measured with an ion electrode in view of the aforementioned problems of the conventional technique, it suffers from a problem that it is not easy to proof the measured values for correcting errors occurring during the culture. This is because, in order to know the present correct ammonia concentration, it is necessary to measure the total ammonia concentration for a sampled culture medium mixed with a strongly alkaline reaction mixture so that the ammonia in the culture medium is converted into non-ionized ammonia ($NH_3$).

Namely, that is because, in usual fermentation, the pH value of the culture medium is within a weakly acidic to weakly alkaline range (about pH 5 to 9), thus a part or substantially all of the ammonia existing in the culture medium exists as ionized, ammonium ion ($NH_4^+$), and therefore it is difficult to obtain the total ammonia concentration (total concentration of $NH_3$ and $NH_4^+$) in the culture medium only by measuring the concentration of non-ionized ammonia ($NH_3$) with the above-mentioned ion electrode. Therefore, the total ammonia concentration cannot be correctly controlled.

SUMMARY

The present invention was accomplished in view of the above problems identified by the present inventors. An object of the present invention is to provide an apparatus for controlling ammonia and a method for controlling ammonia that enable a continuous and arbitrary control of ammonia concentration in the culture medium.

In order to achieve the object mentioned above, the present invention provides the following method and apparatus.

(1) An ammonia-controlling method for controlling ammonia concentration of a culture medium contained in a culture tank, wherein ammonia concentration of the culture medium contained in the culture tank is controlled by using an ammonia-controlling apparatus comprising at least an ammonia feeder that supplies ammonia to the culture tank, an ammonia sensor that responds to non-ionized ammonia in the culture medium contained in the culture tank, and a control part connected to the ammonia feeder and the ammonia sensor, and which method comprises the following steps performed by the control part:

a calibration curve creation step of creating a calibration curve representing relation between non-ionized ammonia concentration of the culture medium contained in the culture tank and a signal from the ammonia sensor, a non-ionized ammonia concentration calculation step of calculating non-ionized ammonia concentration of the culture medium contained in the culture tank from the signal from the ammonia sensor by using the calibration curve, and an ammonia supply direction step of directing the ammonia feeder to supply ammonia to the culture tank when the calculated non-ionized ammonia concentration is lower than a predetermined concentration.

(2) The ammonia-controlling method as mentioned above, further comprising a calibration curve creation step of creating the calibration curve representing relation between non-ionized ammonia concentration of the culture medium contained in the culture tank and the signal from the ammonia sensor.

(3) The ammonia-controlling method as mentioned above, wherein the ammonia-controlling apparatus is further connected to a pH sensor for measuring pH value of the culture medium contained in the culture tank, which method further comprises the following step performed by the control part:

a total ammonia concentration calculation step of calculating total ammonia concentration from the non-ionized ammonia concentration calculated in the non-ionized ammonia concentration calculation step and a pH value measured with the pH sensor on the basis of an ammonia dissociation curve representing an existing ratio of non-ionized ammonia and ammonium ion in the culture medium contained in the culture tank at each pH value, and wherein, in the ammonia supply direction step, the total ammonia concentration is used instead of the non-ionized ammonia concentration.

(4) The ammonia-controlling method as mentioned above, which comprises providing an external ammonia sensor out of the culture tank for measuring non-ionized ammonia concentration, and obtaining a signal from the external ammonia sensor by measuring non-ionized ammonia concentration of a culture medium, which, after collecting from the culture tank, is made sufficiently alkaline for converting ammonium ion into non-ionized ammonia with the external ammonia sensor, as a signal for proofing, and which method further comprises the following step performed by the control part:

a proofing step of proofing the calibration curve so that the non-ionized ammonia concentration calculated from the signal for proofing on the basis of the calibration curve corresponds to the total ammonia concentration calculated in the total ammonia concentration calculation step.

(5) The ammonia-controlling method as mentioned above, wherein the ammonia-controlling apparatus is connected to the external ammonia sensor, and which method further comprises the following step performed by the control part:

a signal for proofing input step of inputting the signal from the external ammonia sensor, as the signal for proofing.

(6) A method for producing a target substance by fermentation comprising culturing a microorganism having an ability to produce the target substance in a culture medium contained in a culture tank, and collecting the target substance from culture, wherein the microorganism is cultured with controlling ammonia concentration of the culture medium by the ammonia-controlling method as mentioned above.

(7) The production method as mentioned above, wherein the target substance is an L-amino acid, an organic acid, a nucleic acid, an alcohol, or a protein.

(8) The production method as mentioned above, wherein the target substance is a basic amino acid selected from the group consisting of L-lysine, L-arginine, and L-histidine.

(9) The production method as mentioned above, which comprises reducing amount of sulfate ions and/or chloride ions used as counter ions of the basic amino acid by adjusting the total ammonia concentration of the culture medium to be within a certain concentration range during at least a part of the total culture process.

(10) The production method as mentioned above, wherein the certain concentration range is 300 mM or lower.

(11) The production method as mentioned above, wherein the certain concentration range is 200 mM or lower.

(12) The production method as mentioned above, wherein the certain concentration range is 100 mM or lower.

(13) An ammonia-controlling apparatus comprising at least an ammonia feeder that supplies ammonia to a culture tank, an ammonia sensor that responds to non-ionized ammonia in the culture medium contained in the culture tank, and a control part connected to the ammonia feeder and the ammonia sensor, wherein:

the ammonia sensor responds to non-ionized ammonia in the culture medium contained in the culture tank, the control part is connected to the ammonia feeder and the ammonia sensor, the control part creates a calibration curve representing relation between non-ionized ammonia concentration of the culture medium and a signal from the ammonia sensor, calculating non-ionized ammonia concentration of the culture medium from the signal from the ammonia sensor by using the calibration curve, and directs the ammonia feeder to supply ammonia to the culture tank when the calculated non-ionized ammonia concentration is lower than a predetermined concentration.

(14) The ammonia-controlling apparatus as mentioned above, which is further connected to a pH sensor for measuring pH value of the culture medium contained in the culture tank, and wherein the control part further calculates total ammonia concentration from the non-ionized ammonia concentration calculated by the non-ionized ammonia concentration calculation means and the pH value measured with the pH sensor on the basis of an ammonia dissociation curve representing an existing ratio of non-ionized ammonia and ammonium ion in the culture medium at each pH value, and the total ammonia concentration is used instead of the non-ionized ammonia concentration.

(15) The ammonia-controlling apparatus as mentioned above, wherein the control part further comprises:

a proofing means for proofing the calibration curve so that the non-ionized ammonia concentration calculated from a signal for proofing on the basis of the calibration curve corresponds to the total ammonia concentration calculated by the total ammonia concentration calculation means, and the signal for proofing is:

a signal obtained with an external ammonia sensor provided out of the culture tank for measuring non-ionized ammonia concentration by preparing the external ammonia sensor, and measuring non-ionized ammonia concentration of a culture medium, which, after collecting from the culture tank, is made sufficiently alkaline for converting ammonium ion into non-ionized ammonia with the external ammonia sensor.

(16) The ammonia-controlling apparatus as mentioned above, which is connected to the external ammonia sensor, and wherein the control part further inputs the signal from the external ammonia sensor, as the signal for proofing.

(17) The ammonia-controlling apparatus as mentioned above, which is configured to keep the total ammonia concentration in a predetermined range.

(18) The ammonia-controlling apparatus as mentioned above, further comprising a user interface.

(19) The ammonia-controlling apparatus as mentioned above, which is configured for real-time controlling of ammonia in a culture medium, preferably for real-time in situ controlling of ammonia in a culture medium.

(20) The ammonia-controlling apparatus as mentioned above, which is adapted to controlling ammonia in a culture medium of more than one culture tanks, optionally 1 to 10 culture tanks.

(21) The ammonia-controlling apparatus as mentioned above, which is adapted to controlling ammonia in the culture medium at intervals of 5 minutes or less, preferably 1 second or less.
(22) The ammonia-controlling apparatus as mentioned above, which is adapted to proofing the calibration curve at intervals of 12 hours or less, preferably 8 hours or less.
(23) The ammonia controlling apparatus as mentioned above, which is adapted to controlling ammonia for at least a part of the culture period or the entire culture period.
(24) A method for producing a target substance by fermentation comprising culturing a microorganism having an ability to produce the target substance in a culture medium contained in a culture tank to produce and accumulate the target substance in the culture medium, wherein total ammonia concentration of the culture medium is adjusted to be within a certain concentration range during at least a part of the total culture process by using the ammonia-controlling apparatus as mentioned above.
(25) The production method as mentioned above, wherein the certain concentration range is 300 mM or lower.
(26) The production method as mentioned above, wherein the certain concentration range is 200 mM or lower.
(27) The production method as mentioned above, wherein the certain concentration range is 100 mM or lower.

According to the present invention, a calibration curve representing relation between the non-ionized ammonia concentration of the culture medium contained in the culture tank and signal from the ammonia sensor (for example, electric voltage) is created, the non-ionized ammonia concentration of the culture medium contained in the culture tank is calculated with a signal from the ammonia sensor on the basis of the calibration curve, and the ammonia feeder is directed to supply ammonia to the culture tank when the calculated non-ionized ammonia concentration is lower than a certain concentration. Therefore, the present invention has effects that sterile operations are enabled for a series of operations for the measurement in a culture tank, and the culture can be performed with continuously and arbitrarily controlling the ammonia concentration in the culture medium without wasting the culture medium.

Further, according to one embodiment of the present invention, the non-ionized ammonia concentration of the culture medium contained in the culture tank is calculated, the pH value of the culture medium contained in the culture tank is measured with a pH sensor, the total ammonia concentration is calculated from the calculated non-ionized ammonia concentration and the measured pH value on the basis of an ammonia dissociation curve stored in a storage part, and when the calculated total ammonia concentration is lower than a predetermined concentration, the ammonia feeder is directed to supply ammonia to the culture tank. Therefore, the present invention has effects that the total ammonia concentration (total concentration of $NH_3$ and $NH_4^+$) of the culture medium can be directly measured from the pH value and the non-ionized ammonia ($NH_3$) concentration on the basis of the ammonia dissociation curve, and thereby the culture can be performed with further correctly controlling the ammonia concentration.

Moreover, according to the present invention, the total ammonia concentration of a sample, collected from the culture tank and suspended in a strongly alkaline reaction mixture so that ammonium ion is converted into non-ionized ammonia, can be investigated by using an external common ammonia measurement apparatus. The non-ionized ammonia concentration in the culture medium can be calculated, from the above total ammonia concentration value and a pH value of the culture medium stored in the aforementioned pH value measurement step, by using the ammonia dissociation equation. The calibration curve representing relation between the non-ionized ammonia concentration and the output of the sensor (electric voltage) can be proofed with it. Therefore, errors generated during the culture can be corrected.

BRIEF DESCRIPTION OF THE DRAWINGS

FIG. 1A shows a flowchart showing an example of the process of the ammonia concentration control according to the present invention.

FIG. 1B shows a flowchart showing another example of the process of the ammonia concentration control according to the present invention.

DETAILED DESCRIPTION

Hereafter, embodiments of the ammonia-controlling apparatus and ammonia-controlling method of the present invention will be explained in detail with reference to the drawings. However, the present invention is not limited to these embodiments.

Figure 2:
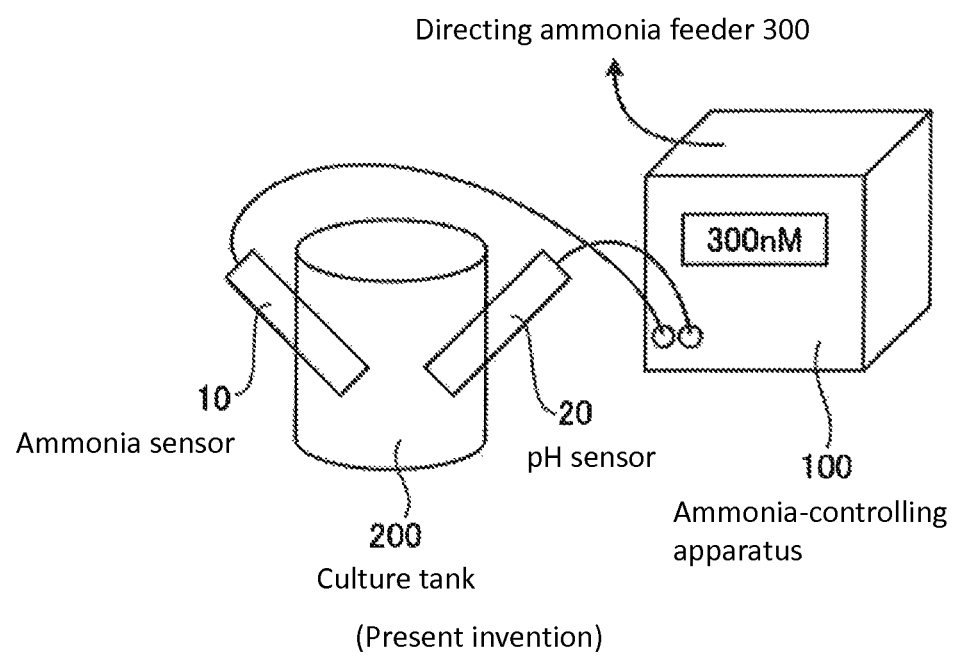
FIG. 2 is a theoretical configurational diagram showing the basic configuration of the present invention.
Figure 3:
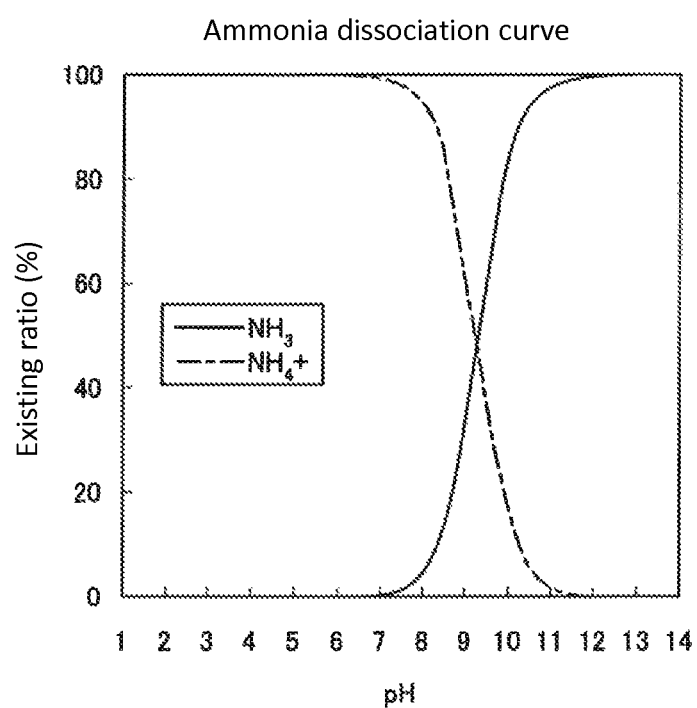
FIG. 3 is a graph showing an example of the ammonia dissociation curve used for the present invention.

Hereafter, outline of the present invention will be explained with reference to FIGS. 1A, 1B, 2, and 3, and then configuration, process, etc. of the present invention will be explained in detail. FIG. 1A is a flowchart showing an example of the process of the ammonia concentration control according to the present invention, FIG. 1B is a flowchart showing another example of the process of the ammonia concentration control according to the present invention, FIG. 2 is a theoretical configurational diagram showing the basic configuration of the apparatus of the present invention, and FIG. 3 is a graph showing an example of the ammonia dissociation curve used for the present invention.

The method of the present invention is an ammonia-controlling method for controlling ammonia concentration of a culture medium contained in a culture tank by using an ammonia-controlling apparatus comprising at least an ammonia feeder that supplies ammonia to the culture tank, an ammonia sensor that responds to non-ionized ammonia in the culture medium contained in the culture tank, and a control part connected to the ammonia feeder and the ammonia sensor. As shown in FIG. 1A, the method of the present invention comprises performing a process with the ammonia-controlling apparatus on the basis of input of a signal from the ammonia sensor that responds to non-ionized ammonia in the culture medium contained in the culture tank, and outputting a direction to the ammonia feeder that supplies ammonia to the culture tank. The term "connected" is sufficient to be functionally connected, and may be connected by a wire or wireless system.

The method of the present invention comprises the following steps performed by the control part, i.e.:

a non-ionized ammonia concentration calculation step of calculating non-ionized ammonia concentration of the culture medium from the signal from the ammonia sensor by using a calibration curve representing relation between non-ionized ammonia concentration of the culture medium and a signal from the ammonia sensor, and an ammonia supply direction step of directing the ammonia feeder to supply ammonia to the culture tank when the calculated non-ionized ammonia concentration is lower than a predetermined concentration.

The method may further comprises a calibration curve creation step of creating a calibration curve representing relation between non-ionized ammonia concentration of the culture medium and a signal from the ammonia sensor. As for the calibration curve, it can be created by providing ammonia solutions at known concentrations, and immersing an electrode in the solutions to plot voltages shown by the electrode.

In the calibration curve creation step, a calibration curve representing relation between the non-ionized ammonia concentration of the culture medium and the signal from the ammonia sensor is created. This creation may comprise reading out a calibration curve from a storage part provided in the ammonia-controlling apparatus, or inputting a calibration curve from the outside.

The ammonia sensor responds to non-ionized ammonia, and is usually a sensor comprising an ammonia selection membrane and an internal electrode. The signal from the ammonia sensor is not particularly limited so long as it is a signal generated by responding to non-ionized ammonia, and a voltage of an internal electrode is usually used. However, it may be converted into another electrical characteristic by using an electric circuit. Further, such an electrical characteristic as voltage may be used as an original analog signal, or as a numerical signal obtained by analog to digital conversion.

A calibration curve can be created by investigating beforehand the relation between such a signal and the non-ionized ammonia concentration in the culture medium. A calibration curve created as described above can be stored in a storage part. The form for the storage is not particularly limited, and the calibration curve may be stored in the form of a table, or an arithmetic equation representing a calibration curve may be stored.

In the non-ionized ammonia concentration calculation step, non-ionized ammonia concentration of the culture medium is calculated from the signal from the ammonia sensor by using the calibration curve. When the calibration curve is stored in the form of a table, the non-ionized ammonia concentration can be determined by reading out a value recorded at the position corresponding to the value of the signal. When the calibration curve is stored as an arithmetic equation, the non-ionized ammonia concentration can be calculated by calculating the value of the equation using the value of the inputted signal.

In the ammonia supply direction step, when the calculated non-ionized ammonia concentration is lower than a predetermined concentration, the ammonia feeder is directed to supply ammonia to the culture tank.

The ammonia feeder is not particularly limited, so long as it can control supply of ammonia to the culture tank on the basis of a direction generated in the ammonia supply direction step. For example, the ammonia feeder is constituted so that, in response to the direction generated in the ammonia supply direction step, an electromagnetic valve of ammonia gas line is opened to supply ammonia.

Ammonia may be gaseous ammonia or aqueous ammonia. Ammonia may also be supplied in the form of an aqueous solution of a compound that generates ammonium ion when it is dissolved, such as ammonium sulfate. Supply rate of ammonia supplied by the ammonia feeder is selected so that the ammonia concentration should not rapidly change, in consideration of size of the culture tank, frequency of directions generated in the ammonia supply direction step, and so forth. The total ammonia concentration of the culture medium is usually controlled to be 1 to 350 mM, more desirably 2.5 to 300 mM, still more desirably 2.5 to 200 mM, still more desirably 3 to 100 mM, still more desirably 3 to 50 mM in terms of ammonia.

The direction may be an output of an electric signal that directly operates such a means as a valve of the ammonia feeder involved in the control of the ammonia supply, or when the ammonia feeder has a communication function, it may be an output of a communication signal for controlling a valve or the like by the communication function.

The ammonia-controlling apparatus of the present invention may be further connected to a pH sensor for measuring pH value of the culture medium contained in the culture tank. In this embodiment, the method of the present invention further comprises the following step performed by the control part, i.e.:

a total ammonia concentration calculation step of calculating the total ammonia concentration from the non-ionized ammonia concentration calculated in the non-ionized ammonia concentration calculation step and the pH value measured with the pH sensor on the basis of an ammonia dissociation curve representing existing ratios of non-ionized ammonia and ammonium ion in the culture medium at each pH value, and in the ammonia supply direction step, the total ammonia concentration is used instead of the non-ionized ammonia concentration.

The relation of the existing ratios of non-ionized ammonia and ammonium ion in the culture medium at each pH value may be theoretically calculated, or actually measured. On the basis of this relation, the dissociation curve can be created.

The dissociation curve created as described above is stored in the storage part. The form of the dissociation curve for the storage is not particularly limited, and it may be stored in the form of a two-dimensional table, or an arithmetic equation representing the dissociation curve may be stored. Furthermore, it may be stored together with the calibration curve to be stored in the calibration curve storage step in the form of a table, or an arithmetic equation representing the dissociation curve in combination with the calibration curve may be created and stored.

The ammonia dissociation curve will be explained with reference to FIG. 3. In FIG. 3, the vertical axis indicates the existing ratio (%) of non-ionized ammonia ($NH_3$) and ammonium ion ($NH_4^+$) in the culture medium contained in the culture tank, and the horizontal axis indicates the pH value of the culture medium contained in the culture tank. The curves shown in the graph of FIG. 3 are the dissociation curves of non-ionized ammonia ($NH_3$) and ammonium ion ($NH_4^+$) at various pH values. As shown in FIG. 3, non-ionized ammonia ($NH_3$) and ammonium ion ($NH_4^+$) exist in substantially equivalent amounts around pH 9, and when the pH value becomes higher, non-ionized ammonia ($NH_3$) increases, whereas ammonium ion ($NH_4^+$) decreases. The non-ionized ammonia and ammonium ion are the same as non-dissociated ammonia ($NH_3$) and dissociated ammonia ($NH_4^+$), respectively.

As descried above, in usual fermentation, the pH value of the culture medium is within a weakly acidic to weakly alkaline range (about pH 5 to 9), thus most part of the ammonia existing in the culture medium exists as ammonium ion ($NH_4^+$), and therefore it has conventionally been impossible to obtain the total ammonia concentration (total concentration of $NH_3$ and $NH_4^+$) in the culture medium only by measuring the concentration of non-ionized ammonia ($NH_3$). However, according to the present invention, the ammonia dissociation curve is created beforehand for the culture medium to be used as a pre-processing, and therefore the total ammonia concentration (total concentration of $NH_3$ and $NH_4$) can be calculated from the non-ionized ammonia ($NH_3$) concentration on the basis of the ammonia dissociation curve.

In the total ammonia concentration calculation step, the total ammonia concentration is calculated from the non-ionized ammonia concentration calculated in the non-ionized ammonia concentration calculation step and a pH value measured with the pH sensor on the basis of the ammonia dissociation curve. When the ammonia dissociation curve is stored in the form of a table, the total ammonia concentration can be determined by reading out a value recorded at an address corresponding to the inputted non-ionized ammonia concentration and pH value. When an arithmetic equation is stored, the total ammonia concentration can be calculated by calculating the value of the equation using the inputted values.

An example of the calculation of the total ammonia concentration is shown in the following (1) to (3).

(1) First, by substituting the voltage measured with the ammonia sensor in the culture tank (for example, 0.5 V) for the corresponding variable in the arithmetic equation representing the calibration curve, the non-ionized ammonia concentration (for example, 30 mM) is calculated.

(2) Then, by substituting the pH value of the culture medium contained in the culture tank measured with the pH sensor (for example, pH 6) for the corresponding variable in the arithmetic equation representing the dissociation curve, the existing ratio of non-ionized ammonia (for example, 40%) is estimated.

(3) By using the estimated existing ratio of non-ionized ammonia (for example, 40%) and the non-ionized ammonia concentration calculated in (1) (for example, 30 mM), calculation is performed, for example, as follows: "30 mM×(100/40)=75 mM", to calculate the total ammonia concentration (75 mM in this case).

In the ammonia supply direction step, when the calculated non-ionized ammonia concentration is lower than a predetermined concentration, the ammonia feeder is directed to supply ammonia to the culture tank. Alternatively, when the total ammonia concentration is lower than a predetermined concentration, the ammonia feeder may be directed to supply ammonia to the culture tank.

The ammonia-controlling apparatus may be further connected to an external ammonia sensor provided out of the culture tank, voltage indicated by the external ammonia sensor for a culture medium collected beforehand from the culture tank and suspended in a strongly alkaline reaction mixture so that the ammonium ion is converted into the non-ionized ammonia may be determined. And the calibration curve may be proofed so that the non-ionized ammonia concentration calculated from the measured voltage by using the calibration curve corresponds to the calculated total ammonia concentration.

The function of automatically calculating the total ammonia concentration on the basis of the ammonia dissociation curve by using an actually measured pH value of the culture medium contained in the culture tank may be used only for the proofing, and the actual ammonia concentration in the culture tank may be controlled on the basis of the non-ionized ammonia ($NH_3$) concentration.

Further, according to the present invention, when the proofing is performed, the calibration curve can be proofed so that the non-ionized ammonia concentration determined from the voltage measured by the external ammonia sensor for a sampled culture medium suspended in a strongly alkaline reaction mixture (for example, NaOH) so that ammonia in the culture medium is converted into non-ionized ammonia corresponds to the total ammonia concentration calculated by the total ammonia concentration calculation using the calibration curve.

Roughly speaking, the apparatus of the present invention has the following basic configuration. That is, the ammonia-controlling apparatus comprising at least an ammonia feeder that supplies ammonia to a culture tank, an ammonia sensor that responds to $NH_3$ in the culture medium contained in the culture tank, and a control part connected to the ammonia feeder and the ammonia sensor. The ammonia feeder may be adapted to supply ammonia to a culture tank. The ammonia sensor adapted to respond to $NH_3$ in the culture medium contained in the culture tank. As shown in FIG. 2, the ammonia-controlling apparatus of the present invention comprises at least an ammonia feeder that supplies ammonia to a culture tank, an ammonia sensor that responds to non-ionized ammonia in culture medium contained in the culture tank, a control part connected to the ammonia feeder and the ammonia sensor, and a storage part. The term "connected" is sufficient to be functionally connected, and may be connected by a wire or wireless system.

The control part comprises:

a calibration curve creation means for creating a calibration curve representing relation between non-ionized ammonia concentration of the culture medium and a signal from the ammonia sensor, a non-ionized ammonia concentration calculation means for calculating the non-ionized ammonia concentration of the culture medium from the signal from the ammonia sensor on the basis of the calibration curve, and an ammonia supply direction means for directing the ammonia feeder to supply ammonia to the culture tank when the non-ionized ammonia concentration is lower than a predetermined concentration.

The control part may comprise:

a storage part configured for storing a predetermined calibration curve, and/or a calibration curve creation means configured for creating a calibration curve representing the relation between non-ionized ammonia concentration of the culture medium and a signal from the ammonia sensor, a non-dissociated ammonia concentration calculation means configured for calculating non-ionized ammonia concentration of the culture medium from the signal from the ammonia sensor by using the calibration curve, and an ammonia supply direction means configured for directing the ammonia feeder to supply ammonia to the culture tank when the calculated non-ionized ammonia concentration is lower than a predetermined concentration.

The control part of the apparatus of the present invention may further comprises a total ammonia concentration calculation means for calculating the total ammonia concentration from the non-ionized ammonia concentration calculated with the non-ionized ammonia concentration calculation means and the pH value measured with the pH sensor on the basis of an ammonia dissociation curve representing existing ratios of non-ionized ammonia and ammonium ion in the culture medium contained in the culture tank at each pH value.

The total ammonia concentration calculation means may be configured for calculating total ammonia concentration from the non-ionized ammonia concentration calculated by the non-ionized ammonia concentration calculation means and the pH value measured with the pH sensor on the basis of an ammonia dissociation curve representing an existing ratio of non-ionized ammonia and ammonium ion in the culture medium at each pH value.

The components of these means are the same as those explained for the steps of the method of the present invention.

The control part may further comprises:
a proofing means configured for proofing the calibration curve so that the non-ionized ammonia concentration calculated from a signal for proofing on the basis of the calibration curve corresponds to the total ammonia concentration calculated by the total ammonia concentration calculation means, and
wherein the proofing means are configured to use a signal for proofing that may be:
a signal obtained with an external ammonia sensor provided out of the culture tank for measuring non-ionized ammonia concentration, and
obtained by measuring non-ionized ammonia concentration of a culture medium, which, after collecting from the culture tank, is made sufficiently alkaline for converting ammonium ion into non-ionized ammonia with the external ammonia sensor.

The control part may be further adapted for inputting the signal from the external ammonia sensor, as the signal for proofing.

The control part may be configured to keep total ammonia in a culture medium within a predetermined range.

The ammonia-controlling apparatus may further comprises a user interface.

The ammonia-controlling apparatus may be configured for real-time controlling of ammonia in a culture medium, preferably for real-time in situ controlling of ammonia in a culture medium.

The ammonia-controlling apparatus may be adapted to controlling ammonia in a culture medium of more than one culture tanks, optionally 1 to 10 culture tanks.

The ammonia-controlling apparatus may be adapted to controlling ammonia in the culture medium at intervals of 5 minutes or less, preferably 1 second or less.

The ammonia-controlling apparatus may be adapted to proofing the calibration curve at intervals of 12 hours or less, preferably 8 hours or less.

The ammonia controlling apparatus may be adapted to controlling ammonia for at least a part of the culture period or the entire culture period.

The real time or real time in-situ used herein means controlling ammonia concentration in a predetermined time, that is, measuring ammonia concentration in the culture tank and supplying ammonia into medium within a predetermined time. For example, as for the time for measuring ammonia, it may adapted to measure at intervals of 5 minutes or less, 3 minutes or less, 1 minute or less, or 30 seconds or less. As for the time for supplying ammonia, it may be adapted to supply at intervals of 1 minute or less, 30 seconds or less, 10 seconds or less, 5 seconds or less, or 1 second or less.

As for the entire culture period, it may be adapted to controlling at intervals of 5 minutes or less, 3 minutes or less, 1 minute or less, 30 seconds or less, or 1 second or less.

The time and interval may be selected depending on a change rate of the concentration of non-ionized ammonia which may occur in the culture medium in the culture tank during the culture, or the total ammonia concentration. For example, it may be adapted to allow the change in the concentration of non-ionized ammonia in the culture medium during the culture to be 0.5 mM or less, 0.2 mM or less, 0.1 mM or less in the measurement interval, or adapted to allow the change in the total ammonia concentration in the culture medium during the culture to be 80 mM or less, 20 mM or less, 10 mM or less in the measurement interval.

Hereafter, an example of the configuration of the ammonia-controlling apparatus will be explained.

[Configuration of Ammonia-Controlling Apparatus 100]

Figure 4:
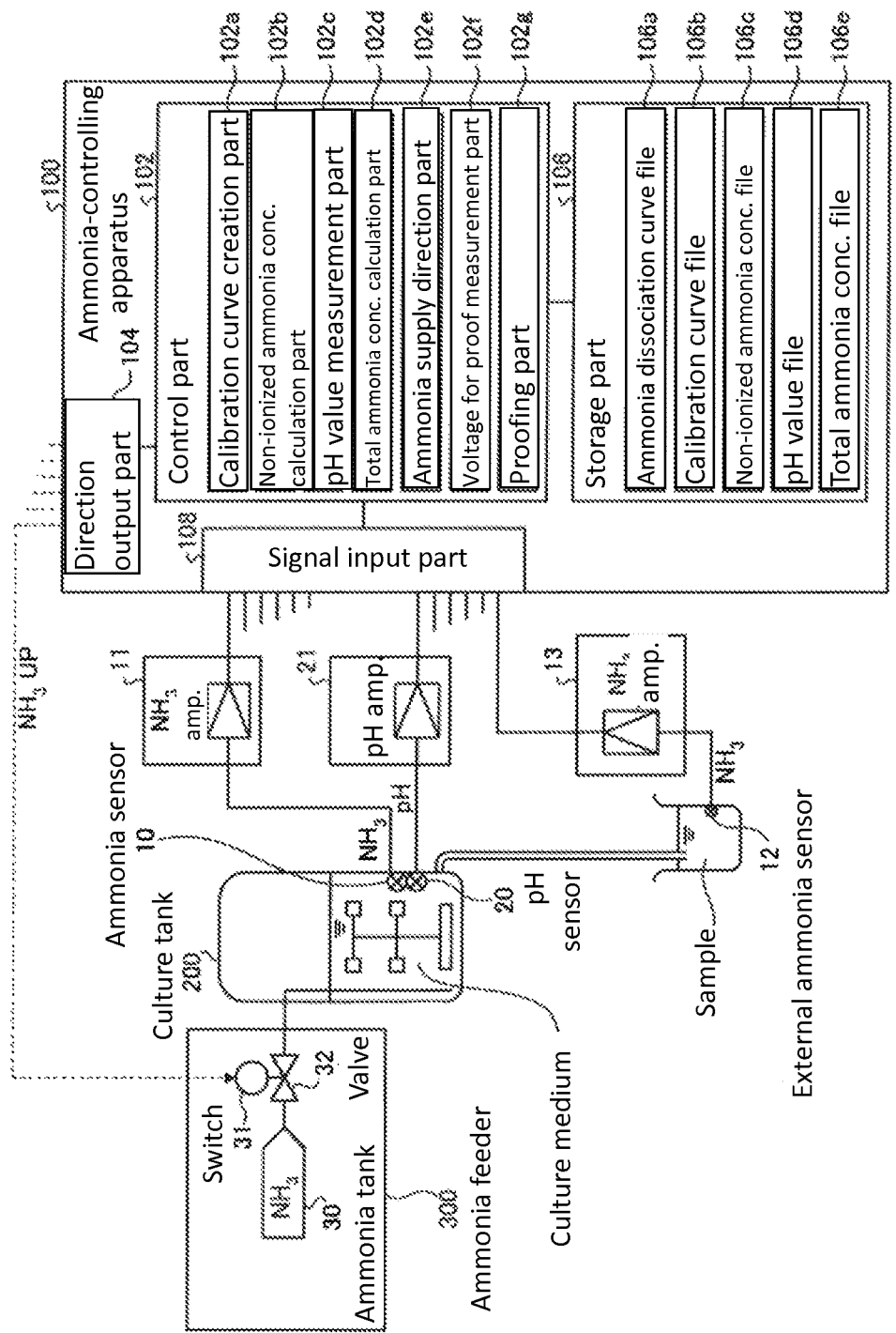
FIG. 4 is a logical block diagram showing an example of the configuration of the ammonia-controlling apparatus 100 according to the present invention.

FIG. 4 is a logical block diagram showing an example of the configuration of the ammonia-controlling apparatus 100 of the present invention, and it conceptually shows only a part of the configuration relating to the present invention.

As shown in FIG. 4, the ammonia-controlling apparatus 100 of the present invention is connected to the culture tank 200, the ammonia feeder 300 that supplies ammonia to the culture tank 200, the ammonia sensor 10 that is inserted into the culture tank 200 and measures an output voltage, and the pH sensor 20 that is inserted into the culture tank 200 and measures pH value. Further, the ammonia-controlling apparatus 100 comprises a control part 102, such as CPU, that integrally controls the whole ammonia-controlling apparatus 100, a control output part 104 that is connected to the ammonia feeder 300 etc., a signal input part 108 that is connected to the ammonia sensor 10, an external ammonia sensor 12, the pH sensor 20, etc., and a storage part 106 that stores various kinds of databases, tables, and so forth, and these parts are communicably connected via arbitrary communication channels.

In FIG. 4, the ammonia feeder 300 comprises at least an ammonia tank 30 that contains ammonia inside, a valve 32 that adjusts amount of ammonia supplied from the ammonia tank 30, and a switch 31 that controls opening and closing of the valve 32. This ammonia feeder 300 has a function of supplying ammonia to the culture tank 200 according to directions sent from the ammonia-controlling apparatus 100.

In FIG. 4, the culture tank 200 contains the culture medium inside, and is connected to the ammonia-controlling apparatus 100 via the ammonia sensor 10 and the pH sensor 20, which are inserted into the culture tank 200. Further, the culture tank 200 is connected to the ammonia feeder 300 via a pipe for supplying ammonia from the ammonia tank 30 or the like. FIG. 4 shows the culture tank 200 connected to a beaker for sampling or the like in which the external ammonia sensor 12 is inserted inside via a pipe for collecting a sample of the culture medium as an example. However, the culture tank 200 may not necessarily be connected to such a beaker, and a user may collect a sample from the culture tank 200, and the external ammonia sensor 12 may be used for a beaker or the like to which the sample is moved.

In FIG. 4, the storage part 106 of the ammonia-controlling apparatus 100 that stores various kinds of databases, tables, files (ammonia dissociation curve file 106a to total ammonia concentration file 106e) comprises a storage means such as fixed disk drive, and stores various kinds of programs, tables, files, databases, and so forth used for various processings.

Among these components of the storage part 106, the ammonia dissociation curve file 106a is an ammonia dissociation curve storage means that stores the ammonia dissociation curve showing existing ratios of non-ionized ammonia and ammonium ion in the culture medium contained in the culture tank 200 at each pH value, which is created by processing performed by the control part 102.

Further, the calibration curve file 106b is a calibration curve storage means that creates and stores a calibration curve representing the relation between the non-ionized ammonia concentration of the culture medium contained in the culture tank 200 and the voltage measured with the ammonia sensor 10.

Further, the non-ionized ammonia concentration file 106c is a non-ionized ammonia concentration storage means that stores the non-ionized ammonia concentration of the culture medium contained in the culture tank 200 measured with the ammonia sensor 10, which is obtained by the non-ionized ammonia concentration calculation part 102b from the voltage measured with the ammonia sensor 10 using the calibration curve.

Further, the pH value file 106d is a pH value storage means that stores pH value of the culture medium contained in the culture tank 200 measured by the pH value measurement part 102c with the pH sensor 20.

Further, the total ammonia concentration file 106e is a total ammonia concentration storage means that stores the total ammonia concentration of the culture medium contained in the culture tank 200 calculated by the total ammonia concentration calculation part 102d from the non-ionized ammonia concentration stored in the non-ionized ammonia concentration file 106c and the pH value stored in the pH value file 106d using the ammonia dissociation curve stored in the ammonia dissociation curve file 106a.

Further, in FIG. 4, the control output part 104 controls communications between the ammonia-controlling apparatus 100 and the ammonia feeder 300. That is, the control output part 104 has a communication function of transmitting a signal for opening and closing the valve 32 by controlling the switch 31 of the ammonia feeder 200 so that the ammonia feeder 300 supplies ammonia to the culture tank 200 in an amount directed by the ammonia-controlling apparatus 100.

Further, in FIG. 4, the signal input part 108 controls the ammonia sensor 10, the external ammonia sensor 12, and the pH sensor 20. The ammonia sensor 10 mentioned above is a sensor for measuring non-ionized ammonia ($NH_3$) concentration among the ammonia contained in the culture medium contained in the culture tank 200, and comprises, for example, an ion electrode or the like. Further, this ammonia sensor 10 may be connected to an $NH_3$ amplifier 11 that amplifies a signal representing the non-ionized ammonia ($NH_3$) concentration measured in the culture tank 200, and transmits it to the signal input part 108. Since the external ammonia sensor 12 and $NH_3$ amplifier 13 are similar to the ammonia sensor 10 and $NH_3$ amplifier 11, explanations thereof are omitted. Further, the pH sensor 20 is a sensor for measuring the pH value of the culture medium contained in the culture tank 200, and comprises, for example, a pH electrode or the like. Further, this pH sensor 20 may be constituted so as to be connected to an pH amplifier 21 that amplifies the signal representing the pH value measured in the culture tank 200, and transmits it to the signal input part 108.

Further, in FIG. 4, the control part 102 has an internal memory for storing control programs, such as OS (Operating System), programs that defines various kinds of processing procedures, and necessary data, and performs information processings for performing various processes with these programs, and so forth. The control part 102 is constituted, in the functional and conceptual sense, so as to comprise the calibration curve creation part 102a, the non-ionized ammonia concentration calculation part 102b, the pH value measurement part 102c, the total ammonia concentration calculation part 102d, the ammonia supply direction part 102e, the voltage for proofing measurement part 102f, and the proof part 102g.

Among these, the calibration curve creation part 102a is a calibration curve creation means that creates a calibration curve representing the relation between the non-ionized ammonia concentration of the culture medium contained in the culture tank 200 and the voltage measured with the ammonia sensor 10.

Further, the non-ionized ammonia concentration calculation part 102b is a non-ionized ammonia concentration calculating means that calculates the non-ionized ammonia concentration of the culture medium contained in the culture tank 200 from the voltage measured with the ammonia sensor 10 by using the calibration curve.

Further, the pH value measurement part 102c is a pH value measuring means for measuring the pH value of the culture medium contained in the culture tank 200 with the pH sensor 20.

Further, the total ammonia concentration calculation part 102d is a total ammonia concentration calculation means for calculating the total ammonia concentration of the culture medium contained in the culture tank 200 from the non-ionized ammonia concentration stored in the non-ionized ammonia concentration file 106c and the pH value stored in the pH value file 106d on the basis of the ammonia dissociation curve stored in the ammonia dissociation curve file 106a.

Further, the ammonia supply direction part 102e is an ammonia supply direction means that directs the ammonia feeder 300 to supply ammonia to the culture tank 200, when the non-ionized ammonia concentration calculated by the non-ionized ammonia concentration calculation part 102b is lower than a predetermined concentration. Further, the ammonia supply direction part 102e may direct the ammonia feeder 300 to supply ammonia to the culture tank 200, when the total ammonia concentration calculated by the total ammonia concentration calculation part 102d is lower than a predetermined concentration.

Further, the voltage for proofing measurement part 102f is a voltage for proofing measurement means for measuring voltage for a sample that is extracted beforehand from the culture tank 200, and suspended in a strongly alkaline reaction mixture (for example, NaOH) so that ammonium ion is converted into non-ionized ammonia with the external ammonia sensor 12.

Further, the proof part 102g is a proof means for proofing a calibration curve stored in the calibration curve file 106b so that the non-ionized ammonia concentration calculated from the voltage measured with the voltage for proofing measurement part 102f by using the calibration curve corresponds to the total ammonia concentration calculated by the total ammonia concentration calculation.

[Processing Performed by Ammonia-Controlling Apparatus 100]

Figure 5:
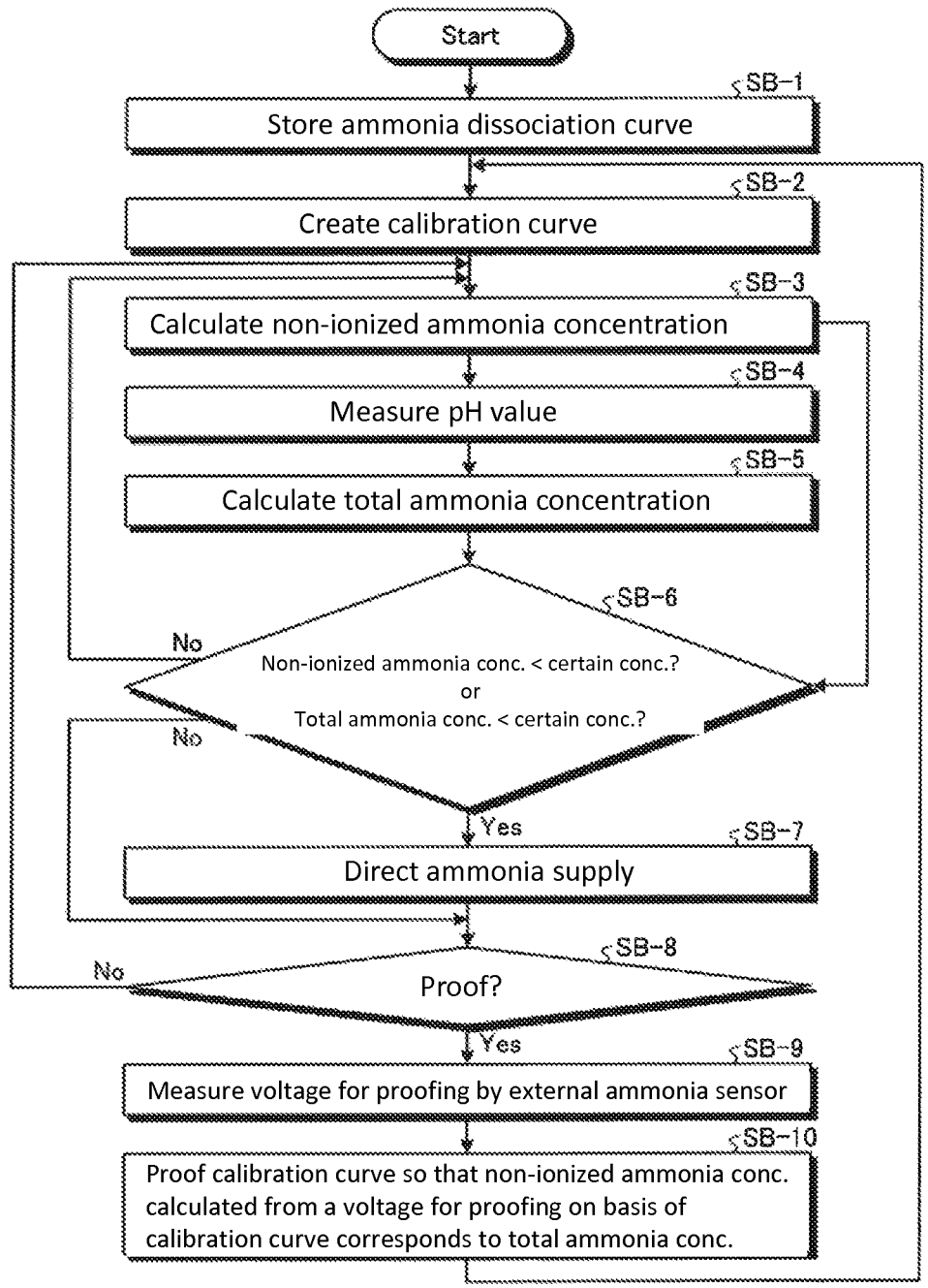
FIG. 5 is a flowchart showing an example of the basic operational processing performed with the ammonia-controlling apparatus 100 according to an embodiment of the present invention.
Figure 6:
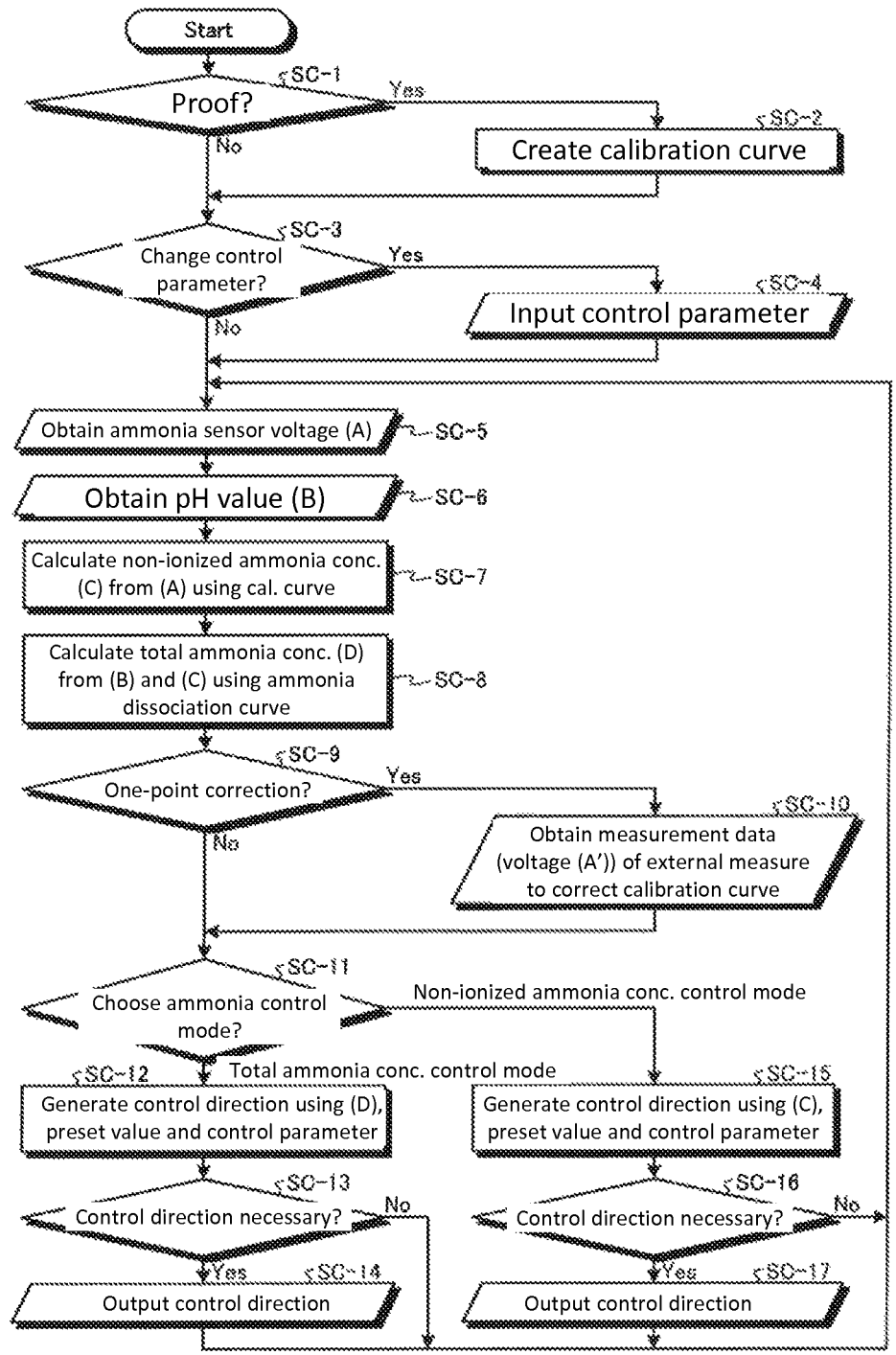
FIG. 6 is a flowchart showing details of an example of the process performed with the ammonia-controlling apparatus 100 according to an embodiment of the present invention.

Hereafter, an example of processing performed by the ammonia-controlling apparatus 100 constituted as described above will be explained in detail with reference to FIGS. 5 and 6. FIG. 5 is a flowchart showing an example of the basic operational processing performed by the ammonia-controlling apparatus 100 according to this embodiment, and FIG. 6 is a flowchart showing details of an example of the processing performed by the ammonia-controlling apparatus 100 according to this embodiment.

[Basic Operational Processing]

First, an example of the basic operational processing performed by the ammonia-controlling apparatus 100 in this embodiment will be explained with reference to FIG. 5.

(Pre-Processing)

As shown in FIG. 5, as a pre-processing, the control part 102 may create an ammonia dissociation curve (refer to FIG. 3) that shows the existing ratio of non-ionized ammonia and ammonium ion in the culture medium contained in the culture tank 200 at each pH value, and store it in the ammonia dissociation curve file 106a (Step SB-1). That is, the control part 102 may create an ammonia dissociation curve by calculating the existing ratios of non-ionized ammonia and ammonium ion at various pH values on the basis of the ammonia dissociation constant, and plotting the calculated values as a graph.

(Main Processing)

Then, the calibration curve creation part 102a creates a calibration curve that represents the relation between the non-ionized ammonia concentration of the culture medium contained in the culture tank 200 and the voltage measured with the ammonia sensor 10 (Step SB-2).

Then, the non-ionized ammonia concentration calculation part 102b calculates the non-ionized ammonia concentration of the culture medium contained in the culture tank 200 from the voltage measured with the ammonia sensor 10 by using the calibration curve (Step SB-3). Then, the process advances to the processing of Step SB-6.

In Step SB-3 mentioned above, after the non-ionized ammonia concentration is calculated by the processing in the non-ionized ammonia concentration calculation part 102b, the processings of Step SB-4 and Step SB-5 may be performed.

The pH value measurement part 102c mentioned above may measure the pH value of the culture medium contained in the culture tank 200 with the pH sensor 20 (Step SB-4). Further, the total ammonia concentration calculation part 102d may calculate total ammonia concentration from the non-ionized ammonia concentration calculated by the non-ionized ammonia concentration calculation part 102b and the pH value measured with the pH value measurement part 102c on the basis of the ammonia dissociation curve stored in the ammonia dissociation curve file 106a (Step SB-5).

Then, the control part 102 judges whether the non-ionized ammonia concentration measured by the non-ionized ammonia concentration calculation part 102b is lower than a predetermined concentration or not (Step SB-6). The control part 102 may judge whether the total ammonia concentration measured by the total ammonia measurement part 102d is lower than a predetermined concentration or not (Step SB-6).

Then, when the control part 102 judges that the non-ionized ammonia concentration measured by the non-ionized ammonia concentration calculation part 102b in Step SB-3 is lower than the predetermined concentration (Step SB-6, Yes), the ammonia supply direction part 102e directs the ammonia feeder 300 to supply ammonia to the culture tank 200 (Step SB-7). The ammonia supply direction part 102e may direct the ammonia feeder 300 to supply ammonia to the culture tank 200, when the control part 102 judges that the total ammonia concentration measured by the total ammonia measurement part 102d is lower than the predetermined concentration (Step SB-6, Yes) (Step SB-7).

On the other hand, when the control part 102 judges that the non-ionized ammonia concentration measured by the non-ionized ammonia concentration calculation part 102b is not lower than the predetermined concentration (Step SB-6, No), the process returns to the processing of Step SB-3.

Further, when the control part 102 judges that the total ammonia concentration measured by the total ammonia measurement part 102d is not lower than the predetermined concentration (Step SB-6, No), the processings of Step SB-8 to Step SB-10 may be performed.

The control part 102 may judge whether the calibration curve created in Step SB-2 is to be proofed or not (Step SB-8). Although FIG. 5 shows an example in which whether the proof processing is started is judged after supply of ammonia is directed (Step SB-6), the judgment may be performed at any time according to user's input, or may be automatically performed for every period set beforehand.

Further, when the control part 102 has judged that proofing is to be performed (Step SB-8, Yes), the voltage for proofing measurement part 102f may measure a voltage with the external ammonia sensor 12 for a sample that is extracted from the culture tank 200 beforehand, and suspended in a strongly alkaline reaction mixture (for example, NaOH) so that ammonium ion is converted into non-ionized ammonia (Step SB-9).

Further, the proof part 102g may proof the calibration curve so that the non-ionized ammonia concentration calculated from the voltage measured by the voltage for proofing measurement part 102f by using the calibration curve stored in the calibration curve file 106b corresponds to the total ammonia concentration calculated by the total ammonia concentration calculation (Step SB-10).

On the other hand, when the control part 102 has judged that the proofing is not to be performed (Step SB-8, No), the process returns to the processing of Step SB-3.

These basic operational processings (Step SB-2 to Step SB-10) are repeatedly performed during the culture. Thereby, the ammonia concentration of the culture medium contained in the culture tank 200 can be controlled, and the culture can be performed with continuously and arbitrarily controlling the ammonia concentration in the culture medium. Now, the explanation of the basic operational processings of the ammonia-controlling apparatus 100 of the present invention is ended.

[Details of Ammonia Control Processing]

Hereafter, details of an example of the processing performed by the ammonia-controlling apparatus 100 according to this embodiment of the present invention will be explained with reference to FIG. 6.

As shown in FIG. 6, the control part 102 judges whether the created ammonia dissociation curve and/or the calculated total ammonia concentration is to be proofed or not (Step SC-1). The content of the processing of this Step SC-1 is the same as that of the processing of Step SB-7 shown in FIG. 5. In addition, as described above, whether this proofing processing is started may be judged at any time according to user's input, or automatically judged for every period set beforehand.

Then, when the control part 102 has judged that proofing is to be performed (Step SC-1, Yes), a calibration curve is created for the culture medium contained in the culture tank 200 (Step SC-2).

The "calibration curve" mentioned above is a relation equation representing the relation between the non-ionized ammonia concentration of the culture medium contained in the culture tank 200 and the voltage measured with the ammonia sensor 10, and in this embodiment, it is used for measuring the non-ionized ammonia concentration (C) from the voltage measured with the ammonia sensor 10 in Step SC-7 and SC-10 described later by using the calibration curve.

On the other hand, when the control part 102 has judged that the proofing is not to be performed (Step SC-1, No), the process advances to the processing of Step SC-3.

Then, the control part 102 judges whether a control parameter for the culture tank 200 is to be changed or not (Step SC-3).

The control parameter mentioned above is, for example, SV (Set Value) value, TC (Time Cycle) value, ON (On Time) value, or the like. The SV value mentioned above is a preset value of the total ammonia concentration or non-ionized ammonia concentration (mM) to be controlled. Further, the TC value represents cycle for judging ammonia supply (second). Further, the ON value represents time (second) for performing the ammonia supply within one cycle. Specifically, when the control parameters are set, for example, as follows: SV value=50 mM, TC value=10 seconds, and ON value=1 second, whether ammonia is to be supplied or not is judged once in 10 seconds, and if the actually measured ammonia concentration is higher than 50 mM, ammonia is not supplied. That is, the electromagnetic valve of the inlet for ammonia gas is maintained to be closed. Further, when the actually measured ammonia concentration is lower than 50 mM, ammonia is supplied for 1 second. That is, the electromagnetic valve is opened.

When the control part 102 has judged that the control parameter is to be changed (Step SC-3, Yes), a new control parameter value is inputted (Step SC-4).

On the other hand, when the control part 102 has judged that the control parameter is not to be changed (Step SC-3, No), the process advances to the processing of Step SC-5.

Then, the non-ionized ammonia concentration calculation part 102*b* incorporates the voltage (A) measured with the ammonia sensor 10 (for example, ion electrode) inserted into the culture tank 200 (Step SC-5). That is, the non-ionized ammonia concentration calculation part 102*b* measures the voltage measured with the ammonia sensor 10.

Then, the pH value measurement part 102*c* incorporates the pH value (B) from the pH electrode of the pH sensor 20 inserted into the culture tank 200 (Step SC-6). That is, the pH value measurement part 102*c* measures the pH value (B) of the culture medium contained in the culture tank 200 with the pH sensor 20.

Then, the non-ionized ammonia concentration calculation part 102*b* calculates the non-ionized ammonia concentration (C) from the voltage (A) incorporated in Step SC-5 by using the calibration curve created in Step SC-2 (Step SC-7). That is, the non-ionized ammonia concentration calculation part 102*b* calculates the non-ionized ammonia concentration (C) of the culture medium contained in the culture tank 200 from the voltage measured with the ammonia sensor 10 by using the calibration curve.

Then, the total ammonia concentration calculation part 102*d* calculates the total ammonia concentration (D) on the basis of the pH value (B) incorporated in Step SC-6, the ammonia concentration (C) calculated in Step SC-7, and the ammonia dissociation curve (refer to FIG. 3) created by the control part 102 as the pre-processing (Step SC-8). That is, the total ammonia concentration calculation part 102*d* calculates the total ammonia concentration (D) of the culture medium contained in the culture tank 200 from the non-ionized ammonia concentration (C) stored in the non-ionized ammonia file 106*c* and the pH value (B) stored in the pH value file 106*d* on the basis of the ammonia dissociation curve stored in the ammonia dissociation curve file 106*a*.

Then, the control part 102 judges whether one-point correction is to be performed or not (Step SC-9).

The "one-point correction" mentioned above is one of the methods for standardization, and is standardizes an object by using a standardization sample of one point. In this embodiment, the standardization sample of one point is the measurement data obtained with an external measurement apparatus (voltage (A')), and the term standardization is used in the same meaning as that of proofing.

When the control part 102 has judged that the one-point correction is to be performed (Step SC-9, Yes), the ammonia concentration for proofing measurement part 102*f* and the proof part 102*g* incorporate the measurement data (voltage (A')) obtained with the external measurement apparatus (external ammonia sensor 12 etc.), and performs the one-point correction for the calibration curve so that the non-ionized ammonia concentration (C') obtained from the measurement data (voltage (A')) by using the calibration curve corresponds to the total ammonia concentration (D) calculated in Step SC-8 (Step SC-10). That is, the voltage for proofing measurement part 102*f* measures the voltage (A') with the external ammonia sensor 12 for a sample extracted from the culture tank 200 beforehand and suspended in a strongly alkaline reaction mixture (for example, NaOH) so that ammonium ion is converted into non-ionized ammonia, and the proof part 102*g* proofs the calibration curve so that the non-ionized ammonia concentration (C') calculated from the voltage (A') measured with the voltage for proofing measurement part 102*f* by using the calibration curve stored in the calibration curve file 106*b* corresponds to the total ammonia concentration (D) calculated by the total ammonia concentration calculation.

On the other hand, when the control part 102 has judged that the one-point correction is not to be performed (Step SC-9, No), the process advances to the processing of Step SC-11.

Then, the control part 102 determines which ammonia control mode is chosen (Step SC-11).

The ammonia control mode mentioned above is, for example, a mode for performing the control with the total ammonia concentration, a mode for performing the control with the non-ionized ammonia concentration, or the like, and in Step SC-11, the control part 102 can choose the total ammonia concentration control mode or the non-ionized ammonia concentration control mode as the ammonia control mode.

Then, when the control part 102 has chosen the total ammonia concentration control mode as the ammonia control mode (Step SC-11, total ammonia concentration control mode), it sets the mode in which the ammonia concentration is controlled on the basis of the total ammonia concentration of the culture medium contained in the culture tank 200. Then, the control part 102 generates directions for control to be sent to the culture apparatus including the ammonia feeder 300 connected to the culture tank 200 etc. by using the total ammonia concentration (D) calculated in Step SC-8 or the total ammonia concentration (D') proofed in Step SC-10, and preset values and control parameters (for example, SV value serving as an index for ammonia concentration control) set in the ammonia-controlling apparatus 100 (Step SC-12).

Then, the control part 102 judges whether the control calculated in Step SC-12 is necessary or not (Step SC-13). For example, the control part 102 judges whether the total ammonia concentration is lower than a predetermined concentration or not.

Then, when the control part 102 has judged that the control direction is necessary (for example, the total ammonia concentration is lower than a predetermined concentration) (Step SC-13, Yes), the ammonia supply direction part 102e outputs a control direction, such as a direction for adding ammonia to the culture tank 200 from an ammonia tank 30 in a directed amount, for the ammonia feeder 300. That is, the ammonia supply direction part 102e operates the switch 31 for changing opening and closing of the valve 32 through the control outputting part 104 to control the opening and closing of the valve 32 so that ammonia is supplied to the culture tank 200 from the ammonia tank 30 in an amount according to the control direction.

On the other hand, when the control part 102 has judged that the control direction is unnecessary (for example, the total ammonia concentration is not lower than the predetermined concentration) (Step SC-13, No), the process returns to the processing of Step SC-5.

When the process returns to Step SC-11, and the control part 102 has chosen the non-ionized ammonia concentration control mode as the ammonia control mode, a mode in which the control is performed on the basis of the non-ionized ammonia concentration of the culture medium contained in the culture tank 200 is set (Step SC-11, non-ionized ammonia concentration control mode). Then, the control part 102 generates control directions for the culture apparatus including the ammonia feeder 300 connected to the culture tank 200 etc, by using the non-ionized ammonia concentration (C) which has been calculated in Step SC-7, preset values and control parameters (for example, SV value serving as an index of ammonia concentration control) set in the ammonia-controlling apparatus 100 (Step SC-15).

Then, the control part 102 judges whether the control calculated in Step SC-15 is necessary or not (Step SC-16). For example, the control part 102 judges whether the non-ionized ammonia concentration is lower than a predetermined concentration.

Then, when the control part 102 has judged that the control direction is necessary (for example, the non-ionized ammonia concentration is lower than a predetermined concentration) (Step SC-16, Yes), the ammonia supply direction part 102e outputs a control direction, such as a direction for adding ammonia to the culture tank 200 from the ammonia tank 30 in a directed amount, for the ammonia feeder 300. That is, the ammonia supply direction part 102e operates the switch 31 for switching opening and closing of the valve 32 through the control outputting part 104 to control the opening and closing of the valve 32 so that ammonia is supplied to the culture tank 200 from the ammonia tank 30 in an amount according to the control direction.

On the other hand, when the control part 102 has judged that the control direction is unnecessary (for example, the non-ionized ammonia concentration is not lower than the predetermined concentration) (Step SC-16, No), the process returns to the processing of Step SC-5.

Now, detailed explanation of an example of the processing of the ammonia-controlling apparatus 100 is finished.

Explanation of this embodiment is also finished.

OTHER EMBODIMENTS

Although an embodiment of the invention has been explained above, the present invention may be implemented as various different embodiments within the technical scope of the present invention defined in the appended claims, besides the embodiment explained above.

For example, although the present invention has been explained above for a case where the ammonia-controlling apparatus 100 performs ammonia control for fermentation performed in the culture tank 200, it can be used for not only fermentation, but also another use such as use in a reaction tank for chemical industry etc.

Further, among the processings explained for the embodiment, all or a part of the processings explained to be automatically performed can also be manually performed, and all or a part of the processings explained to be manually performed can also be performed automatically by known methods.

In addition, the processing procedures, control procedures, specific names mentioned in the aforementioned references and the drawings, information including parameters such as registered data, search conditions etc. for the processings, and database configuration can be arbitrarily changed, unless especially indicated.

Further, the components shown in the drawings for the ammonia-controlling apparatus 100 are schematically shown to indicate the functions thereof, and they may not necessarily be constituted physically as shown in the drawings.

For example, all or a part of the processing functions of the components of the ammonia-controlling apparatus 100, especially the processing functions of the control part 102, can be realized with CPU (Central Processing Unit) and programs to be interpreted and executed by CPU, or with hardware based on wired logic. The programs are recorded in a recording medium described later, and mechanically read by the ammonia-controlling apparatus 100 as required. That is, computer programs for giving commands to CPU to perform various processings by cooperation with OS (Operating System) are stored in the storage part 106, such as ROM and HD. These computer programs are executed by being loaded on RAM, and cooperate with CPU to constitute the control part 102.

Further, the computer programs may be stored in an application program server connected to the ammonia-controlling apparatus 100 through an arbitrary network, and all or a part of them can be downloaded as required.

Further, the programs according to the present invention can also be stored in a computer-readable recording medium. The "recording medium" mentioned above includes arbitrary "portable physical media" such as flexible disk, magneto-optical disk, ROM, EPROM, EEPROM, CD-ROM, MO, and DVD, as well as "communication media" for temporally storing programs such as communication lines and carrier waves used for transmitting the programs through networks, of which typical examples are LAN, WAN, and the internet.

Further, the term "program" means a data processing method described in an arbitrary language or describing method, and the format thereof such as source code and binary code is not limited. In addition, the "program" is not necessarily be limited to those constituted as independent software, but includes those distributed as a plurality of modules or libraries, and those that realize the functions thereof through cooperation with other separate programs, of which typical example is OS (Operating System). In addition, as concrete configurations for reading recording media in the apparatus shown in the embodiment, procedures for reading the programs, procedures for installing them after reading, and so forth, well-known configurations and procedures can be used.

The storage part 106 that stores various kinds of the databases (ammonia dissociation curve file 106a to total ammonia concentration file 106e) and so forth is a storage means comprising a memory device such as RAM and ROM, a fixed disk drive such as hard disk, a flexible disk, an optical disc, or the like, and stores various kinds of programs, tables, databases, files for web pages, etc. used for various processings or presentation on web sites.

Further, the ammonia-controlling apparatus 100 may also be realized by connecting an information processor such as existing personal computers and workstations to an object of the control, and installing software (including programs, data, etc.) for realizing the method of the present invention on the information processor.

Furthermore, specific modes of distribution and integration of the apparatus are not limited to those shown in the drawings, and the apparatus can be constituted by functionally or physically distributing or integrating all or a part of the apparatus in arbitrary units according to various additions of components etc.

The aforementioned ammonia-controlling method and ammonia-controlling apparatus can be used for the following methods. For example, they can be used for a method for producing a target substance by fermentation using a microorganism, specifically, a method of culturing a microorganism having an ability to produce the target substance in a liquid medium contained in a fermentation tank to produce and accumulate the target substance in the medium.

Examples of the target substance referred to in the present invention include L-amino acids, nucleic acids, alcohols, proteins, and so forth. In the present invention, the "L-amino acid" is not particularly limited, so long as it is an L-amino acid that can be accumulated in a medium in fermentation using a microorganism. Although type of the L-amino acid is not particularly limited, examples include basic amino acids such as L-lysine, L-ornithine, L-arginine, L-histidine and L-citrulline, aliphatic amino acids such as L-isoleucine, L-alanine, L-valine, L-leucine and glycine, amino acids which are hydroxy-monoaminocarboxylic acids such as L-threonine and L-serine, cyclic amino acids such as L-proline, aromatic amino acids such as L-phenylalanine, L-tyrosine and L-tryptophan, sulfur-containing amino acids such as L-cysteine, L-cystine and L-methionine, acidic amino acids such as L-glutamic acid, L-aspartic acid, L-glutamine and L-asparagine and acid amides thereof.

The microorganism used in the present invention may have an ability to produce two or more kinds of amino acids. The L-amino acid referred to in the present invention may be a free L-amino acid, or may be a salt such as sulfate, hydrochloride, and carbonate of L-amino acid.

In the present invention, the "nucleic acid" is not particularly limited, so long as it is a nucleic acid that can be accumulated in a medium in fermentation using a microorganism. Examples of the nucleic acid include purine nucleosides, purine nucleotides, and so forth. The purine nucleosides include inosine, xanthosine, guanosine, adenosine, and so forth, and the purine nucleotides include 5'-phosphate esters of the purine nucleosides, for example, inosinic acid, (inosine-5'-phosphate, henceforth also referred to as "IMP"), xanthylic acid (xanthosine-5'-phosphate, henceforth also referred to as "XMP"), guanylic acid (guanosine-5'-monophosphate, henceforth also referred to as "GMP"), adenylic acid (adenosine-5'-monophosphate, henceforth also referred to as "AMP"), and so forth.

In the present invention, the "organic acid" is not particularly limited, so long as it is an organic acid that can be accumulated in a medium in fermentation using a microorganism. Examples of the organic acid include lactic acid, acetic acid, citric acid, gluconic acid, succinic acid, fumaric acid, malic acid, and so forth.

In the present invention, the "alcohol" is not particularly limited, so long as it is an alcohol that can be accumulated in a medium in fermentation using a microorganism. Examples of the alcohol include, for example, ethanol, isobutanol, 1,2-butanediol, 1,3-butanediol, 1,3-propanediol, 1,4-butanediol, glycerol, 2,3-butanediol, and so forth.

Examples of the microorganism usable in the present invention include, specifically, Enterobacteriaceae bacteria belonging to the genus *Escherichia*, *Enterobacter*, *Klebsiella*, *Pantoea*, *Serratia*, *Erwinia*, *Salmonella*, *Morganella*, or the like, coryneform bacteria, *Bacillus* bacteria, *Streptococcus* bacteria, *Saccharomyces* yeasts and so forth. It is preferably a microorganism for which gene substitution is possible.

Examples of the *Escherichia* bacteria include *Escherichia coli* and so forth. When *Escherichia coli* is bred by using genetic engineering techniques, the *E. coli* K12 strain and derivatives thereof, the *Escherichia coli* 1655 strain (ATCC 47076) and the *Escherichia coli* W3110 strain (ATCC 27325), can be used. To obtain the K-12 strain of *Escherichia coli* and the derivative strains, they can be provided from, for example, the American Type Culture Collection (ATCC, Address: P.O. Box 1549, Manassas, Va. 20108, United States of America).

As the *Escherichia* bacteria, those described in the work of Neidhardt et al. (Neidhardt, F. C. et al., *Escherichia coli* and *Salmonella Typhimurium*, American Society for Microbiology, Washington D.C., 1208, table 1), such as *Escherichia coli*, can be utilized. Examples of wild-type strains of *Escherichia coli* include, for example, the K12 strain and derivatives thereof, *Escherichia coli* MG1655 strain (ATCC No. 47076), W3110 strain (ATCC No. 27325), and so forth. They are available from the American Type Culture Collection (ATCC, Address: P.O. Box 1549, Manassas, Va. 20108, United States of America).

Examples of the *Enterobacter* bacteria include *Enterobacter agglomerans*, *Enterobacter aerogenes* and so forth, and examples of the *Pantoea* bacteria include *Pantoea ananatis*. Some species of *Enterobacter agglomerans* have been recently re-classified into *Pantoea agglomerans*, *Pantoea ananatis*, *Pantoea stewartii* or the like, based on the nucleotide sequence analysis of 16S rRNA, etc. Both of the *Enterobacter* bacteria and *Pantoea* bacteria may be used so long as the chosen bacterium is classified into the family Enterobacteriaceae. When a *Pantoea ananatis* strain is bred by a genetic engineering technique, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

The coryneform bacteria are a group of microorganisms defined in Bergey's Manual of Determinative Bacteriology, 8th Ed., p. 599 (1974), and microorganisms classified into such aerobic, Gram-positive and nonacid-fast bacilli which are unable to sporulate can be used. The coryneform bacteria include bacteria which have previously been classified into the genus *Brevibacterium* but are presently united into the genus *Corynebacterium* (Int. J. Syst. Bacteriol. 41:255-260 (1991)), and bacteria belonging to the genus *Brevibacterium* or *Microbacterium*, which closely relates to the genus *Corynebacterium*.

Specific examples of such coryneform bacteria include the following species:
*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

Specific examples of these bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* ATCC 15990
*Corynebacterium melassecola* ATCC 17965
*Corynebacterium efficiens* AJ12340 (FERM BP-1539)
*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* ATCC 13869 (*Corynebacterium glutamicum* ATCC 13869)
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

These strains are available from, for example, the American Type Culture Collection (ATCC) (Address: P.O. Box 1549, Manassas, Va. 2010812301 Parklawn Drive, Rockville, Md. 20852, United States of America). That is, registration numbers are given to each of the strains, and the strains can be ordered by using these registration numbers. The registration numbers of the strains are listed in the catalogue of the American Type Culture Collection (refer to http://www.atcc.org/). The AJ12340 strain was deposited on Oct. 27, 1987 at National Institute of Bioscience and Human Technology, Agency of Industrial Science and Technology, Ministry of Economy, Trade and Industry (currently independent administrative agency, National Institute of Technology and Evaluation, International Patent Organism Depositary, Room No. 120, 2-5-8 Kazusakamatari, Kisarazu-shi, Chiba-ken, 292-0818, Japan) with an accession number of FERM BP-1539 under the provisions of Budapest Treaty. The AJ12418 strain was deposited on Jan. 5, 1989 at National Institute of Bioscience and Human Technology, Agency of Industrial Science and Technology, Ministry of Economy, Trade and Industry (currently independent administrative agency, National Institute of Technology and Evaluation, International Patent Organism Depositary) with an accession number of FERM BP-2205 under the provisions of the Budapest Treaty.

When *Bacillus* bacteria are used, examples thereof include *Bacillus subtilis, Bacillus amyloliquefaciens, Bacillus pumilus*, and so forth.

Examples of *Bacillus subtilis* include *Bacillus subtilis* 168 Marburg strain (ATCC 6051), *Bacillus subtilis* PY79 strain (Plasmid, 1984, 12, 1-9), and so forth. Examples of *Bacillus amyloliquefaciens* include *Bacillus amyloliquefaciens* T strain (ATCC 23842), *Bacillus amyloliquefaciens* N strain (ATCC 23845), and so forth. Examples of *Bacillus pumilus* include *Bacillus pumilus* Gottheil No. 3218 (ATCC 21005) (U.S. Pat. No. 3,616,206), and so forth.

Hereinafter, methods for imparting an L-amino acid- or nucleic acid-producing ability to such parent strains as mentioned above will be described.

To impart the ability to produce an L-amino acid or a nucleic acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include methods of acquiring an auxotrophic mutant, an analogue-resistant strain, or a metabolic regulation mutant, or constructing a recombinant strain so that it overexpresses an L-amino acid or nucleic acid biosynthesis enzyme. In the breeding of an L-amino acid-producing bacteria, one or more of the above described properties such as auxotrophy, analogue-resistance, or metabolic regulation mutation may be imparted. Expression of one or more L-amino acid biosynthesis enzymes may be enhanced. Furthermore, the methods of imparting properties such as an auxotrophic mutation, analogue resistance, or metabolic regulation mutation may be combined with the methods of enhancing the biosynthesis enzymes.

An auxotrophic mutant strain, L-amino acid or nucleic acid analogue-resistant strain, or metabolic regulation mutant strain having an ability to produce an L-amino acid or nucleic acid can be obtained by subjecting a parent strain or wild-type strain to a conventional mutagenesis, such as exposure to X-rays or UV irradiation, or treatment with a mutagen such as N-methyl-N'-nitro-N-nitrosoguanidine, etc., and then selecting those which exhibit an autotrophy, analogue resistance, or metabolic regulation mutation, and which also have the ability to produce an L-amino acid from the obtained mutant stains.

An auxotrophic mutant strain, L-amino acid analogue-resistant strain, or metabolic regulation mutant strain having an ability to produce an L-amino acid can be obtained by subjecting a parent strain or wild-type strain to a conventional mutagenesis, such as exposure to X-rays or UV irradiation, or treatment with a mutagen such as N-methyl-N'-nitro-N-nitrosoguanidine (NTG) or ethyl methanesulfonate (EMS), etc., and then selecting those which exhibit an autotrophy, analogue resistance, or metabolic regulation mutation and which also have the ability to produce an L-amino acid from the obtained mutant stains.

Methods for imparting amino acid-producing ability and obtaining amino acid-producing bacteria will be specifically exemplified below.

(L-Lysine-Producing Bacteria)

L-Lysine-producing bacteria and methods for constructing them are exemplified below.

Examples of strains having L-lysine-producing ability include, for example, L-lysine analogue-resistant strains and metabolic regulation mutant strains. Examples of L-lysine analogue include, but are not limited to, oxalysine, lysine hydroxamate, S-(2-aminoethyl)-L-cysteine (AEC), γ-methyllysine, α-chlorocaprolactam and so forth. Mutant strains having resistance to these lysine analogues can be obtained by subjecting a bacterium belonging to the family Enterobacteriaceae or a coryneform bacterium to a conventional artificial mutagenesis treatment. Specific examples of L-lysine-producing bacteria include *Escherichia coli* AJ11442 (FERM BP-1543, NRRL B-12185, see Japanese Patent Application Laid-open No. 56-18596 and U.S. Pat. No. 4,346,170), *Escherichia coli* VL611 strain (Japanese Patent Application Laid-open No. 2000-189180), and so forth. As an L-lysine-producing *Escherichia coli*, the WC196 strain may also be used (see International Publication WO96/17930).

Furthermore, an L-lysine-producing bacterium can also be constructed by increasing activity of an L-lysine biosynthesis system enzyme. Increase of activity of such an enzyme can be attained by increasing copy number of the gene coding for the enzyme in cells, or by modifying an expression control sequence thereof. Increase of copy number of a gene coding for an enzyme of L-lysine biosynthesis system in cells and modification of an expression control sequence can be attained in the same manner as that for the gltP and gltS genes described below.

Examples of genes coding for L-lysine biosynthetic enzymes include genes coding for enzymes of the diaminopimelate pathway such as dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO96/40934 for all the foregoing genes), phosphoenolpyruvate carboxylase gene (ppc) (Japanese Patent Application Laid-open No. 60-87788), aspartate aminotransferase gene (aspC) (Japanese Patent Publication (Kokoku) No. 6-102028), diaminopimelate epimerase gene (dapF) (Japanese Patent Application Laid-open No. 2003-135066), and aspartate semialdehyde dehydrogenease gene (asd) (WO00/61723), and genes coding for enzymes of the aminoadipic acid pathway such as homoaconitate hydratase gene (Japanese Patent Application Laid-open No. 2000-157276). In addition, the parent strain may show an increased level of expression of the gene involved in energy efficiency (cyo) (EP 1170376 A), the gene coding for nicotinamide nucleotide transhydrogenase (pntAB) (U.S. Pat. No. 5,830,716), the ybjE gene coding for a protein having L-lysine excretion activity (WO2005/073390), the gene coding for glutamate dehydrogenase (gdhA) (Gene 23:199-209 (1983)), or an arbitrary combination of these. Abbreviations for the genes are shown in the parentheses. Among the aforementioned genes, the ybjE gene is preferred.

It is known that the wild-type dihydrodipicolinate synthase derived from *Escherichia coli* suffers from feedback inhibition by L-lysine, and it is known that the wild-type aspartokinase derived from *Escherichia coli* suffers from suppression and feedback inhibition by L-lysine. Therefore, when the dapA and lysC genes are used, these genes are preferably genes coding for mutant enzymes desensitized to the feedback inhibition by L-lysine.

Examples of DNA encoding a mutant dihydrodipicolinate synthetase desensitized to the feedback inhibition by L-lysine include a DNA encoding such a protein having an amino acid sequence in which the histidine residue at the position 118 is replaced by tyrosine residue. Examples of DNA encoding a mutant aspartokinase desensitized to the feedback inhibition by L-lysine include a DNA encoding an AKIII having an amino acid sequence in which the threonine residue at the position 352, the glycine residue at the position 323, and the methionine residue at the position 318 are replaced by isoleucine, asparagine and isoleucine residues, respectively (for these mutants, see U.S. Pat. Nos. 5,661,012 and 6,040,160). Such mutant DNAs can be obtained by site-specific mutagenesis using PCR or the like.

Wide host-range plasmids RSFD80, pCAB1, and pCABD2 are known as plasmids containing a mutant dapA gene encoding a mutant dihydrodipicolinate synthase and a mutant lysC gene encoding a mutant aspartokinase (U.S. Pat. No. 6,040,160). The *Escherichia coli* JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently independent administrative agency, National Institute of Technology and Evaluation, International Patent Organism Depositary) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a conventional method.

Furthermore, L-amino acid-producing bacteria may have reduced activity of an enzyme that catalyzes a reaction branching off from an L-amino acid biosynthesis pathway and producing another compound, or may be deficient in such an activity, or they may have reduced activity of an enzyme that negatively acts on L-amino acid synthesis or accumulation, or may be deficient in such an activity. Examples of such enzymes involved in the L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

It is preferred that expressions of both the cadA and ldcC genes encoding lysine decarboxylase are decreased in order to decrease or delete the lysine decarboxylase activity. Expression of the both genes can be decreased by, for example, the method described in WO2006/078039.

In order to reduce or eliminate activities of these enzymes, a mutation may be introduced into genes of the enzymes on a genome by a usual mutagenesis method or gene recombination technique so that intracellular activities of the enzymes are reduced or eliminated. Such introduction of a mutation can be achieved by, for example, using genetic recombination to eliminate the genes coding for the enzymes on the genome or to modify an expression control sequence such as a promoter or the Shine-Dalgarno (SD) sequence. It can also be achieved by introducing a mutation for amino acid substitution (missense mutation), a stop codon (nonsense mutation), or a frame shift mutation for adding or deleting one or two nucleotides into regions coding for the enzymes on the genome, or partially or totally deleting the genes (J. Biol. Chem., 272:8611-8617 (1997)). The enzymatic activities can also be decreased or eliminated by constructing a gene coding for a mutant enzyme, of which coding region is totally or partially deleted, and substituting it for a normal gene on a genome by homologous recombination or the like, or by introducing a transposon or IS factor into the gene.

For example, in order to introduce a mutation that decreases or eliminates the activities of the above-mentioned enzymes by genetic recombination, the following methods are used. A mutant gene is prepared by modifying a partial sequence of an objective gene so that it does not encode an enzyme that can function normally, and then a bacterium belonging to the family Enterobacteriaceae can be transformed with a DNA containing the mutant gene to cause recombination of a corresponding gene on the genome with the mutant gene to substitute the mutant gene for the objective gene on the genome. Examples of such gene substitution using homologous recombination include methods of using a linear DNA such as the method called Red-driven integration (Datsenko, K. A, and Wanner, B. L., Proc. Natl. Acad. Sci. USA, 97:6640-6645 (2000)), and the method utilizing the Red driven integration in combination with an excisive system derived from λ phage (Cho, E. H., Gumport, R. I., Gardner, J. F., J. Bacteriol., 184:5200-5203 (2002)) (refer to WO2005/010175), a method of using a plasmid containing a temperature sensitive replication origin (U.S. Pat. No. 6,303,383, Japanese Patent Application Laid-open No. 05-007491), and so forth. Furthermore, such site-specific mutagenesis based on gene substitution using homologous recombination can also be performed by using a plasmid which is not able to replicate in a host.

Preferred examples of L-lysine-producing bacteria include *Escherichia coli* WC196ΔcadAΔldcC/pCABD2 (WO2006/078039). The strain was constructed by introducing the plasmid pCABD2 containing lysine biosynthesis genes (U.S. Pat. No. 6,040,160) into the WC196 strain having disrupted cadA and ldcC genes, which encode lysine decarboxylase. The WC196 strain was bred from the W3110 strain, which was derived from *Escherichia coli* K-12, by replacing the wild type lysC gene on the chromosome of the W3110 strain with a mutant lysC gene encoding a mutant aspartokinase III in which threonine at position 352 was replaced with isoleucine, resulting in desensitization of the feedback inhibition thereof by L-lysine (U.S. Pat. No. 5,661,012), and conferring AEC resistance to the resulting strain (U.S. Pat. No. 5,827,698). The WC196 strain was designated *Escherichia coli* AJ13069, deposited at the National Institute of Bioscience and Human-Technology, Agency of Industrial Science and Technology (currently independent administrative agency, National Institute of Technology and Evaluation, International Patent Organism Depositary, Room No. 120, 2-5-8 Kazusakamatari, Kisarazu-shi, Chiba-ken, 292-0818, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698). The WC196ΔcadAΔldcC strain itself is also a preferred L-lysine-producing bacterium. The WC196ΔcadAΔldcC was designated AJ110692, and deposited at National Institute of Bioscience and Human Technology, Agency of Industrial Science and Technology (currently, the independent administrative agency, National Institute of Technology and Evaluation, International Patent Organism Depositary, Room No. 120, 2-5-8 Kazusakamatari, Kisarazu-shi, Chiba-ken, 292-0818, Japan) on Oct. 7, 2008 as an international deposit and assigned an accession number of FERM BP-11027.

The plasmid pCABD2 contains a mutant dapA gene derived from *Escherichia coli* and coding for a dihydrodipicolinate synthase (DDPS) having a mutation for desensitization to the feedback inhibition by L-lysine, a mutant lysC gene derived from *Escherichia coli* and coding for aspartokinase III having a mutation for desensitization to the feedback inhibition by L-lysine, the dapB gene derived from *Escherichia coli* and coding for dihydrodipicolinate reductase, and the ddh gene derived from *Brevibacterium lactofermentum* and coding for diaminopimelate dehydrogenase.

The procedures described above for enhancing gene expression of the enzymes involved in the L-lysine biosynthesis, and the methods for reducing the enzymatic activities can similarly be applied to genes coding for other L-amino acid biosynthesis enzymes.

(L-Tryptophan-Producing Bacteria)

Examples of L-tryptophan-producing bacteria and parent strains usable for deriving them include, but are not limited to, strains belonging to the genus *Escherichia*, such as *E. coli* JP4735/pMU3028 (DSM10122) and JP6015/pMU91 (DSM10123) which are deficient in tryptophanyl-tRNA synthetase encoded by mutant trpS gene (U.S. Pat. No. 5,756,345), *E. coli* SV164 (pGH5) having a serA allele encoding phosphoglycerate dehydrogenase desensitized to the feedback inhibition by serine and a trpE allele encoding anthranilate synthase desensitized to feedback inhibition by tryptophan (U.S. Pat. No. 6,180,373), *E. coli* AGX17 (pGX44) (NRRL B-12263) and AGX6(pGX50)aroP (NRRL B-12264) deficient tryptophanase (U.S. Pat. No. 4,371,614), *E. coli* AGX17/pGX50, pACKG4-pps in which a phosphoenolpyruvate-producing ability is enhanced (WO97/08333, U.S. Pat. No. 6,319,696), and so forth. L-Tryptophan-producing bacteria belonging to the genus *Escherichia* which have enhanced activity of the protein encoded by the yedA or yddG gene may also be used (U.S. Patent Published Applications 2003/0148473 A1 and 2003/0157667 A1).

Examples of L-tryptophan-producing bacteria and parent strains usable for deriving them also include strains in which one or more activities of the following enzymes are enhanced: anthranilate synthase (trpE), phosphoglycerate dehydrogenase (serA), and tryptophan synthase (trpAB). The anthranilate synthase and phosphoglycerate dehydrogenase both are subject to feedback inhibition by L-tryptophan and L-serine, and therefore a mutation desensitizing the enzymes to the feedback inhibition may be introduced into these enzymes. Specific examples of strains having such a mutation include *E. coli* SV164 which harbors desensitized anthranilate synthase and a transformant strain SV164 obtained by introducing into the *E. coli* SV164 the plasmid pGH5, which contains a mutant serA gene encoding a feedback inhibition-desensitized phosphoglycerate dehydrogenase (WO94/08031).

Examples of L-tryptophan-producing bacteria and parent strains usable for deriving them also include a strain which has enhanced activity of 3-phosphoserine phosphatase (serB) (U.S. Pat. No. 4,371,614), a strain which has enhanced activity of phosphoenolpyruvate carboxykinase (pckA) (WO2004/090125), and a strain in which enzymes of the glyoxylic acid pathway are constitutively expressed (WO2005/103275).

L-Tryptophan, L-phenylalanine, and L-tyrosine are all aromatic amino acids and share a common biosynthesis pathway. Examples of the genes encoding the biosynthesis enzymes for these aromatic amino acids include deoxyarabino-heptulosonate phosphate synthase (aroG), 3-dehydroquinate synthase (aroB), shikimic acid dehydratase (aroE), shikimate kinase (aroL), 5-enolpyruvylshikimate-3-phosphate synthase (aroA), and chorismate synthase (aroC) (European Patent Publication No. 763127 A). It is known that these genes are controlled by the tyrosine repressor (tyrR), and therefore activity of an aromatic amino acid biosynthesis enzyme may also be increased by deleting the tyrR gene (see European Patent Publication No. 763127 A). The abbreviations in parentheses after the enzyme names represent the gene names (the same shall apply to the same occasions hereafter).

In order to enhance the productivity of each of the target aromatic amino acids, biosynthesis system of an amino acid other than the target amino acid may be attenuated. For example, when the target amino acid is L-tryptophan, biosynthetic pathways of L-phenylalanine and/or L-tyrosine may be attenuated (U.S. Pat. No. 4,371,614).

In the present invention, the term "increase of activity of enzyme" corresponds to, for example, an increased number of enzyme molecules per cell, increased specific activity per enzyme molecule, and so forth. For example, the activity can be increased by increasing expression amount of the gene of the enzyme. Intracellular activity of an enzyme is preferably increased to be higher than that of a non-modified strain, for example, a wild-type strain, of the microorganism.

Furthermore, 3-deoxy-D-arabinoheptulosonate-7-phosphate synthetase (aroF, aroG) is subject to feedback inhibition by aromatic amino acids. Therefore, the enzyme may be modified so that it is desensitized to the feedback inhibition. An aromatic L-amino acid-producing bacterium can be obtained by, for example, introducing a mutant aroF in which the L-aspartic acid residue at the position 147 or the L-serine residue at the position 181 from the N-terminus is replaced by another amino acid, or by introducing a mutant aroG gene in which one of the L-aspartic acid residue at the position 146, the L-methionine residue at the position 147, the L-proline at position 150 and the L-alanine residue at the position 202, or both the L-methionine residue at the position 157 and the L-alanine residue at the position 219 from the N-terminus are replaced by other amino acid(s) (EP0488424).

Examples of L-tryptophan-producing bacteria and parent strains usable for deriving them also include strains into which the tryptophan operon containing a gene encoding inhibition-desensitized anthranilate synthase has been introduced (Japanese Patent Application Laid-open Nos. 57-71397, 62-244382, U.S. Pat. No. 4,371,614). Moreover, L-tryptophan-producing ability may be imparted by enhancing expression of a gene which encodes tryptophan synthase in the tryptophan operon (trpBA). Tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

As coryneform bacteria, Corynebacterium glutamicum AJ12118 (FERM BP-478, Japanese Patent No. 01681002), which is resistant to sulfaguanidine, the coryneform bacterium introduced with the tryptophan operon (Japanese Patent Application Laid-open No. 63-240794), and the coryneform bacterium introduced with a gene coding for shikimate kinase derived from a coryneform bacterium (Japanese Patent Application Laid-open No. 01-994749) can be used.

(L-Phenylalanine-Producing Bacteria)

Examples of L-phenylalanine-producing bacteria and parent strains usable for deriving them include, but are not limited to, strains belonging to the genus Escherichia, such as E. coli AJ12739 (tyrA::Tn10, tyrR) (VKPM B-8197), E. coli HW1089 (ATCC 55371) harboring a mutant pheA34 gene (U.S. Pat. No. 5,354,672), E. coli MWEC101-b (Korean Patent No. 8903681), E. coli NRRL B-12141, NRRL B-12145, NRRL B-12146, and NRRL B-12147 (U.S. Pat. No. 4,407,952). Also, as a parent strain, E. coli K-12 [W3110 (tyrA)/pPHAB (FERM BP-3566), E. coli K-12 [W3110 (tyrA)/pPHAD] (FERM BP-12659), E. coli K-12 [W3110 (tyrA)/pPHATerm] (FERM BP-12662) and E. coli K-12[W3110 (tyrA)/pBR-aroG4, pACMAB] named as AJ12604 (FERM BP-3579) may also be used (EP 488424 B1). Furthermore, L-phenylalanine-producing bacteria belonging to the genus Escherichia with an enhanced activity of the protein encoded by the yedA gene or the yddG gene may also be used (U.S. Patent Published Applications No. 2003/0148473 A1 and 2003/0157667 A1).

As phenylalanine-producing coryneform bacteria, the Cornebacterium glutamicum BPS-13 (FERM BP-1777), K77 (FERM BP-2062), and K78 (FERM BP-2063) (European Patent Publication No. 331145 A, Japanese Patent Application Laid-open No. 02-303495), of which phosphoenolpyruvate carboxylase or pyruvate kinase activity is reduced, tyrosine-auxotrophic strain (Japanese Patent Application Laid-open No. 05-049489), and so forth can be used.

A bacterium which efficiently produces phenylalanine can also be obtained by modifying a bacterium so that it incorporates by-products, for example, by increasing the expression amount of the L-tryptophan uptake gene, tnaB or mtr, or the L-tyrosine uptake gene, tyrP (EP 1484410).

(L-Tyrosine-Producing Bacteria)

Examples of tyrosine-producing bacteria include Escherichia bacteria with a desensitized prephenate dehydratase gene (tyrA) (European Patent Publication No. 1616940 A).

(L-Valine-Producing Bacteria)

Examples of L-valine-producing bacteria and parent strains usable for deriving L-valine-producing bacteria include, but are not limited to, strains which have been modified to overexpress the ilvGMEDA operon (U.S. Pat. No. 5,998,178). It is preferred that the region in the ilvGMEDA operon which is required for attenuation is removed so that expression of the operon is not attenuated by the L-valine that is produced. Furthermore, it is preferred that the ilvA gene in the operon is disrupted so that threonine deaminase activity is decreased.

Examples of parent strains usable for deriving L-valine-producing bacteria also include mutant strains with aminoacyl t-RNA synthetase having a mutation (U.S. Pat. No. 5,658,766). For example, E. coli VL1970, which has a mutation in the ileS gene encoding isoleucine tRNA synthetase, can be used. E. coli VL1970 was deposited at the Russian National Collection of Industrial Microorganisms (VKPM) (1 Dorozhny proezd., 1 Moscow 117545, Russia) on Jun. 24, 1988 under an accession number VKPM B-4411.

Further, mutants requiring lipoic acid for growth and/or lacking $H^+$-ATPase can also be used as parent strains (WO96/06926).

Examples of L-valine-producing bacteria of coryneform bacteria include, for example, strains modified so that expression of a gene encoding an L-valine biosynthetic enzyme is enhanced. Examples of the L-valine biosynthesis enzyme include enzymes encoded by genes present on the ilvBNC operon, that is, acetohydroxy acid synthetase encoded by ilvBN and isomero-reductase encoded by ilvC (WO00/50624). Since the ilvBNC operon is subject to expression regulation by L-valine and/or L-isoleucine and/or L-leucine, it is desirable to eliminate attenuation to avoid expression suppression by L-valine that is produced.

L-Valine-producing ability can be imparted to coryneform bacteria and L-valine-producing ability of coryneform bacteria can be improved by decreasing or eliminating activity of at least one kind of enzyme which is involved in a metabolic pathway that decreases L-valine production. For example, decrease of the activity of threonine dehydratase involved in the L-leucine synthesis, or activity of an enzyme that involved in D-panthothenate synthesis is contemplated (WO00/50624).

Examples of methods for imparting L-valine-producing ability also include imparting resistance to an amino acid analogue or the like.

Examples include, for example, mutant strains which are auxotrophic for L-isoleucine and L-methionine, and resistant to D-ribose, purine ribonucleoside or pyrimidine ribonucleoside, and have an ability to produce L-valine (FERM P-1841, FERM P-29, Japanese Patent Publication No. 53-025034), mutant strains resistant to polyketides (FERM P-1763, FERM P-1764, Japanese Patent Publication No. 06-065314), and mutant strains resistant to L-valine in a medium containing acetic acid as the sole carbon source and sensitive to pyruvic acid analogues (β-fluoropyruvic acid etc.) in a medium containing glucose as the sole carbon source (FERM BP-3006, BP-3007, Japanese Patent No. 3006929).

An example of a gene involved in the synthesis of branched chain amino acids is the ilvGMEDA operon, and this operon is subject to expression control (attenuation) by L-valine and/or L-isoleucine and/or L-leucine. Therefore, productivity of a microorganism for these L-amino acids can be improved by introducing into the microorganism the ilvGMEDA operon in which the region required for the attenuation is removed or mutated.

(L-Isoleucine-Producing Bacteria)

Examples of L-isoleucine-producing bacteria and parent strains usable for deriving L-isoleucine-producing bacteria include, but are not limited to, mutants having resistance to 6-dimethylaminopurine (Japanese Patent Application Laid-open No. 5-304969), mutants having resistance to an isoleucine analogue such as thiaisoleucine and isoleucine hydroxamate, and mutants having resistance to DL-ethionine and/or arginine hydroxamate (Japanese Patent Application Laid-open No. 5-130882). In addition, recombinant strains transformed with genes encoding proteins involved in L-isoleucine biosynthesis, such as threonine deaminase and acetohydroxy acid synthase, can also be used as the parent strains (Japanese Patent Application Laid-open No. 2-458, French Patent No. 0356739, and U.S. Pat. No. 5,998,178).

Examples of L-isoleucine-producing strains of coryneform bacteria include the coryneform bacterium in which the brnE gene coding for a branched chain amino acid excretion protein is amplified (Japanese Patent Application Laid-open No. 2001-169788), the coryneform bacterium imparted with L-isoleucine-producing ability by protoplast fusion with an L-lysine-producing bacterium (Japanese Patent Application Laid-open No. 62-74293), the coryneform bacterium in which homoserine dehydrogenase is enhanced (Japanese Patent Application Laid-open No. 62-91193), the threonine hydroxamete resistant strain (Japanese Patent Application Laid-open No 62-195293), α-ketomalonic acid resistant strain (Japanese Patent Application Laid-open No. 61-15695), and the methyl lysine resistant strain (Japanese Patent Application Laid-open No. 61-15696).

(L-Leucine-Producing Bacteria)

Examples of L-leucine-producing bacteria and parent strains usable for deriving L-leucine-producing bacteria include, but are not limited to, Escherichia bacteria, such as E. coli strains resistant to leucine (for example, the strain 57 (VKPM B-7386, U.S. Pat. No. 6,124,121)) or leucine analogues including β-2-thienylalanine, 3-hydroxyleucine, 4-azaleucine and 5,5,5-trifluoroleucine (Japanese Patent Publication No. 62-34397 and Japanese Patent Application Laid-open No. 8-70879); E. coli strains obtained by the genetic engineering method described in WO96/06926; and E. coli H-9068 (Japanese Patent Application Laid-open No. 8-70879).

L-Leucine-producing bacteria may also be improved by enhancing expression of one or more genes involved in L-leucine biosynthesis. Examples of such genes include genes of the leuABCD operon, which are preferably represented by a mutant leuA gene coding for isopropylmalate synthase desensitized to feedback inhibition by L-leucine (U.S. Pat. No. 6,403,342). In addition, L-leucine-producing bacteria may also be improved by enhancing the expression of one or more genes coding for proteins which excrete L-amino acid from the bacterial cell. Examples of such genes include the b2682 and b2683 genes (ygaZH genes) (EP 1239041 A2).

Examples of L-leucine-producing strains of coryneform bacteria include the 2-thiazolealanine and β-hydroxyleucine-resistant strains (Japanese Patent Application Laid-open No. 8-266295), the valine analogue-resistant strain (Japanese Patent Application Laid-open No. 63-248392), the valine auxotrophic strain (Japanese Patent Publication No. 38-4395), the S-(2-aminoethyl)-L-cysteine (AEC) resistant strain (Japanese Patent Publication No. 51-37347), and the phenylalanine, valine and isoleucine auxotrophic strain (Japanese Patent Publication No. 54-36233).

(L-Glutamic Acid-Producing Bacteria)

Preferred examples of L-glutamic acid-producing bacteria include, for example, strains in which expression of a gene encoding an L-glutamic acid biosynthetic enzyme is enhanced. Examples of such genes include, but are not limited to, genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth.

Examples of strains which have been modified so that expression of the citrate synthetase gene, the phosphoenolpyruvate carboxylase gene, the isocitrate dehydrogenase gene, the pyruvate dehydrogenase gene, and/or the glutamate dehydrogenase gene is enhanced include those disclosed in EP 1078989 A, EP 955368 A, EP 952221 A and EP 1033407 A.

The modification for imparting L-glutamic acid-producing ability may also be attained by decreasing or eliminating activity of an enzyme that catalyzes a reaction branching off from the L-glutamic acid biosynthesis pathway and producing a compound other than L-glutamic acid. Examples of such an enzyme that catalyzes a reaction branching off from the L-glutamic acid biosynthesis pathway and producing a compound other than L-glutamic acid include isocitrate lyase, α-ketoglutarate dehydrogenase, acetohydroxy acid synthase, acetolactate synthase, formate acetyltransferase, lactate dehydrogenase, glutamate decarboxylase, 1-pyrroline-5-carboxylate dehydrogenase, and so forth.

For example, in order to decrease the α-ketoglutarate dehydrogenase activity, a modification may be performed by using the sucA (odhA) gene coding for the E1o subunit of the enzyme. Examples of strains with decreased α-ketoglutarate dehydrogenase activity include, for example, the following strains:

*Brevibacterium lactofermentum* ΔS strain (WO95/34672)
*Brevibacterium lactofermentum* AJ12821 (FERM BP-4172; French Patent No. 9401748)
*Brevibacterium flavum* AJ12822 (FERM BP-4173; French Patent No. 9401748)
*Corynebacterium glutamicum* AJ12823 (FERM BP-4174; French Patent No. 9401748)
*Pantoea ananatis* AJ13601 (FERM BP-7207)
*Klebsiella planticola* AJ13410 (FERM BP-6617)
*Pantoea ananatis* AJ13355 (FERM BP-6614)

*Pantoea ananatis* AJ13356 is deficient in α-ketoglutarate dehydrogenase activity as a result of disruption of the αKGDH-E1 subunit gene (sucA). This strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depositary as *Enterobacter agglomerans*, it is described as *Pantoea ananatis* in this specification.

Furthermore, the ability to produce L-glutamic acid can also be imparted to coryneform bacteria by a method of amplifying the yggB gene (NCgl 1221; NP_600492. Reports small-conductance. [gi:19552490], WO2006/070944), or a method of introducing a mutant yggB gene in which a mutation is introduced into the coding region.

Examples of other methods for imparting or enhancing L-glutamic acid-producing ability include a method of imparting resistance to an organic acid analogue, a respiratory chain inhibitor, etc., and a method of imparting sensitivity to a cell wall synthesis inhibitor. Examples of such methods include the method of imparting resistance to monofluoroacetic acid (Japanese Patent Application Laid-open No. 50-113209), the method of imparting resistance to adenine or thymine (Japanese Patent Application Laid-open No. 57-065198), the method of attenuating urease (Japanese Patent Application Laid-open No. 52-038088), the method of imparting resistance to malonic acid (Japanese Patent Application Laid-open No. 52-038088), the method of imparting resistance to benzopyrones or naphthoquinones (Japanese Patent Application Laid-open No. 56-1889), the method of imparting resistance to HOQNO (Japanese Patent Application Laid-open No. 56-140895), the method of imparting resistance to α-ketomalonic acid (Japanese Patent Application Laid-open No. 57-2689), the method of imparting resistance to guanidine (Japanese Patent Application Laid-open No. 56-35981), the method of imparting sensitivity to penicillin (Japanese Patent Application Laid-open No. 4-88994), and so forth.

Specific examples of such resistant strains include the following strains:

*Brevibacterium flavum* AJ3949 (FERM BP-2632; Japanese Patent Application Laid-open No. 50-113209)
*Corynebacterium glutamicum* AJ11628 (FERM P-5736; Japanese Patent Application Laid-open No. 57-065198)
*Brevibacterium flavum* AJ11355 (FERM P-5007; Japanese Patent Application Laid-open No. 56-1889)
*Corynebacterium glutamicum* AJ11368 (FERM P-5020; Japanese Patent Application Laid-open No. 56-1889)
*Brevibacterium flavum* AJ11217 (FERM P-4318; Japanese Patent Application Laid-open No. 57-2689)
*Corynebacterium glutamicum* AJ11218 (FERM P-4319; Japanese Patent Application Laid-open No. 57-2689)
*Brevibacterium flavum* AJ11564 (FERM BP-5472; Japanese Patent Application Laid-open No. 56-140895)
*Brevibacterium flavum* AJ11439 (FERM BP-5136; Japanese Patent Application Laid-open No. 56-35981)
*Corynebacterium glutamicum* H7684 (FERM BP-3004; Japanese Patent Application Laid-open No. 04-88994)
*Brevibacterium lactofermentum* AJ11426 (FERM P-5123; Japanese Patent Application Laid-open No. 56-048890)
*Corynebacterium glutamicum* AJ11440 (FERM P-5137; Japanese Patent Application Laid-open No. 56-048890)
*Brevibacterium lactofermentum* AJ11796 (FERM P-6402; Japanese Patent Application Laid-open No. 58-158192)

(L-Threonine-Producing Bacteria)

Preferred examples of L-threonine-producing bacteria include bacteria belonging to the family Enterobacteriaceae in which an activity of L-threonine biosynthesis system enzyme is enhanced. Examples of genes coding for L-threonine biosynthetic enzymes include the aspartokinase III gene (lysC), aspartate semialdehyde dehydrogenase gene (asd), aspartokinase I gene (thrA), homoserine kinase gene (thrB), and threonine synthase gene (thrC) encoded by the thr operon. Two or more kinds of these genes may be introduced. The genes coding for the L-threonine biosynthetic enzymes may be introduced into an Enterobacteriaceae bacterium with decreased threonine decomposition. Examples of the *Escherichia* bacterium with decreased threonine decomposition include, for example, the TDH6 strain which is deficient in threonine dehydrogenase activity (Japanese Patent Application Laid-open No. 2001-346578), and so forth.

The activities of the L-threonine biosynthetic enzymes are inhibited by the end product L-threonine, and therefore L-threonine biosynthetic enzymes are preferably modified so as to be desensitized to the feedback inhibition by L-threonine when constructing L-threonine producing strains. The above-described thrA, thrB and thrC genes constitute the threonine operon which has an attenuator structure. The expression of the threonine operon is inhibited by isoleucine and threonine in the culture medium and also repressed by attenuation. This attenuation can be eliminated or reduced by removing a leader sequence or attenuator in the attenuation region (Lynn, S. P., Burton, W. S., Donohue, T. J., Gould, R. M., Gumport, R. I., and Gardner, J. F. J., Mol. Biol. 194:59-69 (1987); WO02/26993; WO2005/049808).

The native promoter present in the upstream region of the threonine operon may be replaced by a non-native promoter (WO98/04715), or the threonine operon may be constructed so that expression of the threonine biosynthetic genes is controlled by the repressor and promoter of λ-phage (European Patent No. 0593792). Furthermore, mutant *Escherichia* bacteria that are desensitized to feedback inhibition by L-threonine can be obtained by selecting strains resistant to α-amino-β-hydroxyisovaleric acid (AHV).

It is preferable that the copy number of the modified feedback inhibition-resistant threonine operon is increased, or the expression of the modified operon is increased by connecting it to a potent promoter in the host. The copy number can be increased by using, in addition to amplification using a plasmid, transposon, Mu-phage, or the like so that the operon is transferred onto the chromosome.

The gene encoding aspartokinase III (lysC) is preferably modified so that the enzyme is desensitized to feedback inhibition by L-lysine. Such a modified feedback inhibition-resistant lysC gene can be obtained by the method described in U.S. Pat. No. 5,932,453.

L-Threonine-producing bacteria can also be preferably obtained by enhancing expression of genes involved in the glycolytic pathway, TCA cycle, or respiratory chain, or genes that regulate expression of these genes, or genes involved in sugar uptake, besides the L-threonine biosynthetic enzyme genes. Examples of these genes that are effective for L-threonine production include the transhydrogenase gene (pntAB, European Patent No. 733712), phosphoenolpyruvate carboxylase gene (pepC, WO95/06114), phosphoenolpyruvate synthase gene (pps, European Patent No. 877090), and pyruvate carboxylase gene derived from coryneform bacterium or Bacillus bacterium (WO99/18228, European Patent Publication No. 1092776 A).

L-Threonine-producing bacteria can also be preferably obtained by enhancing expression of a gene that imparts L-threonine resistance and/or a gene that imparts L-homoserine resistance, or by imparting L-threonine resistance and/or L-homoserine resistance to the host bacterium. Examples of the genes that impart the above-mentioned resistance include the rhtA gene (Res. Microbiol. 154:123-135 (2003)), rhtB gene (European Patent Publication No. 0994190 A), rhtC gene (European Patent Publication No. 1013765 A), yfiK gene, and yeaS gene (European Patent Publication No. 1016710 A). Exemplary methods for imparting L-threonine resistance to a host bacterium include those described in European Patent Publication No. 0994190 A and WO90/04636.

*E. coli* VKPM B-3996 (U.S. Pat. No. 5,175,107) can be exemplified as an L-threonine-producing bacterium. The strain VKPM B-3996 was deposited on Nov. 19, 1987 at the Russian National Collection of Industrial Microorganisms (VKPM), GNII Genetika (Russia, 117545 Moscow 1, Dorozhny proezd, 1) under the registration number VKPM B-3996. The VKPM B-3996 strain contains the plasmid pVIC40 (WO90/04636) which was obtained by inserting the threonine biosynthetic genes (threonine operon, thrABC) into a wide host range plasmid vector pAYC32 containing the streptomycin resistance marker (Chistorerdov, A. Y., and Tsygankov, Y. D., Plasmid, 16, 161-167 (1986)). In pVIC40, aspartokinase I-homoserine dehydrogenase I encoded by the thrA gene in the threonine operon is desensitized to feedback inhibition by L-threonine.

*E. coli* VKPM B-5318 (refer to European Patent No. 0593792) can also be exemplified as a preferred L-threonine-producing bacterium. The VKPM B-5318 strain was deposited at the Russian National Collection of Industrial Microorganisms (VKPM) GNII Genetika on May 3, 1990 under a registration number of VKPM B-5318. The VKPM B-5318 strain is prototrophic with regard to L-isoleucine, and harbors a recombinant plasmid DNA constructed so that the threonine operon, i.e., threonine biosynthesis genes, deficient in the attenuator region, which is an originally contained transcription regulation region, is located downstream from the λ phage-derived temperature-sensitive C1 repressor, PR-promoter, and the gene coding for N-terminal of Cro protein, and the expression of the threonine biosynthesis genes is regulated by the repressor and the promoter derived from λ phage.

(L-Arginine-Producing Bacteria)

Examples of L-arginine-producing bacteria and parent strains usable for deriving L-arginine-producing bacteria include, but are not limited to, *Escherichia* bacterial strains, such as *E. coli* strain 237 (VKPM B-7925) (U.S. Patent Published Application No. 2002/058315 A1) and its derivative strains harboring mutant N-acetylglutamate synthase (Russian Patent Application No. 2001112869), *E. coli* strain 382 (VKPM B-7926) (EP 1170358 A1), and an arginine-producing strain transformed with the argA gene encoding N-acetylglutamate synthetase (EP 1170361 A1).

Examples of L-arginine-producing bacteria and parent strains usable for deriving L-arginine-producing bacteria also include strains in which the expression of one or more genes encoding an L-arginine biosynthetic enzyme is enhanced. Examples of such genes include the N-acetylglutamyl phosphate reductase gene (argC), ornithine acetyl transferase gene (argJ), N-acetylglutamate kinase gene (argB), acetylornithine transaminase gene (argD), ornithine carbamoyl transferase gene (argF), argininosuccinic acid synthetase gene (argG), argininosuccinic acid lyase gene (argH), and carbamoyl phosphate synthetase gene (carAB).

Examples of coryneform bacteria that have the L-arginine-producing ability include, but are not limited to, wild-type strains of coryneform bacteria; coryneform bacteria resistant to certain agents including sulfa drugs, 2-thiazolealanine, α-amino-β-hydroxyvaleric acid and so forth; coryneform bacteria exhibiting L-histidine, L-proline, L-threonine, L-isoleucine, L-methionine, or L-tryptophan auxotrophy in addition to the resistance to 2-thiazolealanine (Japanese Patent Application Laid-open No. 54-44096); coryneform bacteria resistant to ketomalonic acid, fluoromalonic acid, or monofluoroacetic acid (Japanese Patent Application Laid-open No. 57-18989); coryneform bacteria resistant to argininol (Japanese Patent Application Laid-open No. 62-24075); coryneform bacteria resistant to X-guanidine (X represents a derivative of fatty acid or aliphatic chain, Japanese Patent Application Laid-open No. 2-186995) and so forth. The coryneform bacterium deficient in the L-arginine repressor (U.S. Patent Published Application No. 20020045233) and the coryneform bacterium of which glutamate dehydrogenase activity is increased (European Patent Publication No. 1057893 A) are also strains suitable for L-arginine production.

Specifically, the following strains can be exemplified: *Brevibacterium flavum* AJ11169 (BP-6892), *Corynebacterium glutamicum* AJ12092 (FERM BP-6906), *Brevibacterium flavum* AJ11336 (FERM BP-6893), *Brevibacterium flavum* AJ11345 (FERM BP-6894), and *Brevibacterium lactofermentum* AJ12430 (FERM BP-2228). The AJ11169 and the AJ12092 strains are the 2-thiazolealanine resistant strains described in Japanese Patent Application Laid-open No. 54-44096, the AJ11336 strain is the argininol- and sulfadiazine-resistant strain described in Japanese Patent Publication No. 62-24075, the AJ11345 strain is the strain which is resistant to argininol, 2-thiazolealanine, and sulfaguanidine, and exhibits histidine auxotrophy described in Japanese Patent Publication No. 62-24075, and the AJ12430 strain is the octylguanidine- and 2-thiazolealanine-resistant strain described in Japanese Patent Application Laid-open No. 2-186995.

*Corynebacterium glutamicum* AJ12092 (FERM BP-6906) was deposited on Sep. 29, 1983 at National Institute of Bioscience and Human Technology, Agency of Industrial Science and Technology (currently independent administrative agency, National Institute of Technology and Evaluation, International Patent Organism Depositary, Room No. 120, 2-5-8 Kazusakamatari, Kisarazu-shi, Chiba-ken, 292-0818, Japan) with an accession number of FERM P-7273, and the original deposit was converted to an international deposit based on Budapest Treaty on Oct. 1, 1999, and it was assigned an accession number of FERM BP-6906.

Examples of *Escherichia* bacteria having L-arginine-producing ability include *Escherichia coli* introduced with the argA gene (see Japanese Patent Application Laid-open No. 57-5693), and the *Escherichia coli* 237 strain, which is an L-arginine-producing derivative of acetic acid-utilizing mutant strain (Russian Patent Application No. 2000117677). The strain 237 was deposited at Russian National Collection of Industrial Microorganisms (VKPM) GNII Genetika under the accession number VKPM B-7925 since Apr. 10, 2000, and the original deposit was converted to an international deposit based on Budapest Treaty, on May 18, 2001. The *Escherichia coli* 382 strain having a mutation for resistance to the feedback inhibition by L-arginine, which is a derivative of the 237 strain (Japanese Patent Application Laid-Open No. 2002-017342) can also be used. The *Escherichia coli* 382 strain was deposited at the Russian National Collection of Industrial Microorganisms with a number of VKPM B-7926 on Apr. 10, 2000, and the deposit was converted to an international deposition based on the Budapest Treaty on May 18, 2001.

Examples of *Serratia* bacteria having L-arginine-producing ability include *Serratia marcescens* deficient in ability to decompose L-arginine, and exhibiting resistance to arginine antagonists and canavanine and auxotorophy for lysine (see Japanese Patent Application Laid-open No. 52-8729).

(L-Histidine-Producing Bacteria)

Examples of parent strains usable for deriving L-histidine-producing bacteria include, but are not limited to, *Escherichia* bacterial strains, such as *E. coli* strain 24 (VKPM B-5945, RU2003677), *E. coli* strain 80 (VKPM B-7270, RU2119536), *E. coli* NRRL B-12116 to B-12121 (U.S. Pat. No. 4,388,405), *E. coli* H-9342 (FERM BP-6675), *E. coli* H-9343 (FERM BP-6676) (U.S. Pat. No. 6,344,347), *E. coli* H-9341 (FERM BP-6674) (EP 1085087), and *E. coli* AI80/pFM201 (U.S. Pat. No. 6,258,554).

Examples of parent strains usable for deriving L-histidine-producing bacteria also include strains in which expression of one or more genes encoding L-histidine biosynthetic enzymes are enhanced. Examples of such genes include the ATP phosphoribosyltransferase gene (hisG), phosphoribosyl AMP cyclohydrolase gene (hisI), phosphoribosyl-ATP pyrophosphohydrolase gene (hisIE), phosphoribosylformimino-5-aminoimidazole carboxamide ribotide isomerase gene (hisA), amidotransferase gene (hisH), histidinol phosphate aminotransferase gene (hisC), histidinol phosphatase gene (hisB), histidinol dehydrogenase gene (hisD), and so forth.

It is known that the L-histidine biosynthetic enzymes encoded by hisG and hisBHAFI are inhibited by L-histidine, and therefore the ability to produce L-histidine can also be efficiently enhanced by introducing a mutation which confers resistance to the feedback inhibition into the gene coding for ATP phosphoribosyltransferase (hisG) (Russian Patent Nos. 2003677 and 2119536).

Specific examples of strains having L-histidine-producing ability include *E. coli* FERM-P 5038 and 5048 which have been transformed with a vector carrying a DNA encoding an L-histidine biosynthetic enzyme (Japanese Patent Application Laid-open No. 56-005099), *E. coli* strains transformed with a gene encoding a protein involved in amino acid export (EP 1016710 A), *E. coli* 80 strain which is resistant to sulfaguanidine, DL-1,2,4-triazole-3-alanine, and streptomycin (VKPM B-7270, Russian Patent No. 2119536), and so forth.

(L-Cysteine-Producing Bacteria)

Examples of parent strains usable for deriving L-cysteine-producing bacteria include, but are not limited to, strains belonging to the genus *Escherichia*, such as *E. coli* JM15 which is transformed with different cysE alleles encoding feedback-resistant serine acetyltransferases (U.S. Pat. No. 6,218,168, Russian Patent Application No. 2003121601), *E. coli* W3110 with overexpressed genes encoding proteins which promote excretion of substances toxic to cells (U.S. Pat. No. 5,972,663), *E. coli* strains with reduced cysteine desulfohydrase activity (Japanese Patent Application Laid-open No. 11-155571), *E. coli* W3110 with increased activity of a positive transcriptional regulator for cysteine regulon encoded by the cysB gene (WO01/27307A1), and so forth.

(L-Serine-Producing Bacteria)

Examples of parent strains usable for deriving L-serine-producing bacteria include coryneform bacteria in which the phosphoserine phosphatase gene is amplified (Japanese Patent Application Laid-open Nos. 2001-275689 and 11-253187), coryneform bacteria having D-3-phosphoglycerate dehydrogenase desensitized to inhibition, which is derived from coryneform bacteria having L-serine-producing ability and resistant to azaserine or β-(2-thienyl)-DL-alanine (Japanese Patent Application Laid-open No. 11-266881), and serine-producing coryneform bacteria resistant to azaserine or thienylalanine, and deficient in serine decomposition ability (Japanese Patent Application Laid-open No. 10-248588).

Methods for imparting nucleic acid-producing ability to a microorganism and nucleic acid-producing bacteria will be exemplified below.

A microorganism having an ability to produce a nucleic acid can be obtained by imparting, for example, purine nucleoside auxotrophy or resistance to a drug such as purine analogue to such bacteria as described above (refer to Japanese Patent Publication Nos. 38-23099, 54-17033, 55-45199, 57-14160, 57-41915 and 59-42895). For example, a *Bacillus* bacterium having auxotrophy or drug resistance can be obtained by a treatment with a mutatgen which is used for usual mutagenesis treatment such as N-methyl-N'-nitro-N-nitrosoguanidine (NTG) or ethyl methanesulfonate (EMS).

Examples of *Bacillus* bacteria that produce a purine nucleoside include the followings.

As a specific example of inosine-producing strain belonging to the genus *Bacillus*, the *Bacillus subtilis* KMBS16 strain can be used. This strain is derived from the known *Bacillus subtilis* trpC2 strain (168 Marburg), wherein the purR gene encoding the purine operon repressor (purR::spc), the purR gene encoding succinyl-AMP synthase (purA::erm), and the deoD gene encoding purine nucleoside phosphorylase (deoD::kan) are disrupted (Japanese Patent Application Laid-open No. 2004-242610, U.S. Patent Published Application No. 2004166575 A1). The *Bacillus subtilis* AJ3772 strain (FERM P-2555, Japanese Patent Application Laid-open No. 62-014794) and so forth may also be used.

Examples of *Bacillus* bacteria having an ability to produce guanosine include the *Bacillus* bacterium having increased IMP dehydrogenase activity (Japanese Patent Application Laid-open No. 3-58787), *Bacillus* bacterium obtained by introducing a vector including a gene which confers resistance to purine analogues or decoyinine into an adenine auxotrophic mutant (Japanese Patent Publication No. 4-28357), and so forth.

Examples of *Bacillus* bacteria that produce a purine nucleotide include the followings.

As inosinic acid-producing *Bacillus* bacteria, inosine-producing strains of *Bacillus subtilis* which have attenuated phosphatase activity have been reported (Uchida, K. et al., Agr. Biol. Chem., 1961, 25, 804-805; Fujimoto, M., Uchida, K., Agr. Biol. Chem., 1965, 29, 249-259). Examples of guanylic acid-producing bacteria include mutants of *Bacillus* bacteria which have adenine auxotrophy, resistance to decoyinine or methionine sulfoxide and an ability to produce 5'-guanylic acid (guanosine-5'-monophosphate, henceforth also referred to as "GMP") (Japanese Patent Publication No. 56-12438).

Furthermore, a xanthylic acid-producing bacterium can be constructed by the method used to breed coryneform bacteria, a typical example of which is *Corynebacterium ammoniagenes*. For example, by obtaining a PRPP amidotransferase-enhanced strain (Japanese Patent Application Laid-open No. 8-168383), an aliphatic amino acid-resistant strain (Japanese Patent Application Laid-open No. 4-262790), or a dehydroproline-resistant strain (South Korean Patent Unexamined Publication No. 2003-56490), a xanthylic acid-producing bacterium can be constructed.

Moreover, exemplary methods for breeding *Bacillus* bacteria which have an ability to produce a purine-derived substance also include enhancing activity of an enzyme which is involved in purine biosynthesis which is common to the biosynthesis of purine nucleosides and purine nucleotides, i.e., purine biosynthesis enzyme, in bacterial cells.

Examples of the enzyme involved in the purine biosynthesis include, for example, phosphoribosyl pyrophosphate amidotransferase, phosphoribosyl pyrophosphate synthetase (PRPP synthetase [EC: 2.7.6.1]), and so forth.

Some of the catabolites produced by metabolism of sugar sources such as glucose that flow into the pentose phosphate pathway are converted into ribose-5-phosphate via ribulose-5-phosphate. From the biosynthesized ribose-5-phosphate, phosphoribosyl pyrophosphate (PRPP) is produced, which is an indispensable precursor for purine nucleoside, histidine and tryptophan biosyntheses. Specifically, ribose-5-phosphate is converted into PRPP by phosphoribosyl pyrophosphate synthetase. Therefore, an ability to produce purine-derived substance can be imparted to a *Bacillus* bacterium or the ability of the bacterium can be enhanced by modifying the bacterium so that the activity of phosphoribosyl pyrophosphate synthetase thereof is increased.

The activity of the phosphoribosyl pyrophosphate synthetase can be measured by, for example, the method of Switzer et al. (Methods Enzymol., 1978, 51, 3-11) or the method of Roth et al. (Methods Enzymol., 1978, 51, 12-17). A *Bacillus* bacterium in which the activity of phosphoribosyl pyrophosphate synthetase is increased can be produced by, for example, increasing expression of a gene encoding the phosphoribosyl pyrophosphate synthetase in a *Bacillus* bacterium according to a method of using a plasmid or integrating the gene into a chromosome, which can be performed in the same manner as that of the method described in Japanese Patent Application Laid-open No. 2004-242610.

On the other hand, when PRPP, which is an indispensable precursor for purine nucleoside, histidine and tryptophan biosyntheses, is produced, some of it is converted into purine nucleotides and purine nucleosides by the enzymes involved in the purine biosynthesis. Examples of genes encoding such enzymes include the genes of the purine operon from *Bacillus subtilis*, specifically, genes of the purEKB-purC(orf)QLF-purMNH(J)-purD operon (Ebbole D. J. and Zalkin H., J. Biol. Chem., 1987, 262, 17, 8274-87) (at present, also called purEKBCSQLFMNHD, *Bacillus subtilis* and Its Closest Relatives, Editor in Chief: A. L. Sonenshein, ASM Press, Washington D.C., 2002, Genbank Accession No. NC_000964), and the genes of the pur regulon from *Escherichia coli* (*Escherichia* and *Salmonella*, Second Edition, Editor in Chief: F. C. Neidhardt, ASM Press, Washington D.C., 1996).

Accordingly, by enhancing expression of these genes, an ability to produce a purine-derived substance can also be imparted or enhanced. In addition, genes of the purine operon which can be used for the present invention are not limited to these, and genes derived from other microorganisms, animals and plants may also be used.

Examples of the method for increasing expression of the purine operon include increasing expression of genes of the purine operon in a *Bacillus* bacterium by a method of using a plasmid, integrating the genes into a chromosome, or the like.

The second method for increasing expression of the purine operon includes replacing a native promoter of the purine operon with a stronger promoter, and replacing the −35 or −10 region of the native promoter with a consensus sequence.

For example, in *Bacillus subtilis* (*B. subtilis* 168 Marburg strain, ATCC 6051), the −35 sequence of the purine operon is a consensus sequence (TTGACA), but the −10 sequence is TAAGAT, which differs from the consensus sequence TATAAT (Ebbole, D. J. and H. Zalikn, J. Biol. Chem., 1987, 262, 8274-8287). Therefore, by replacing the −10 sequence (TAAGAT) with a consensus sequence, or by approximating the −10 sequence (TAAGAT) close to the consensus sequence, it can be changed into TATAAT, TATGAT or TAAAAT, and thereby the transcriptional activity of the purine operon can be increased. A promoter sequence can be replaced by the same method as that of the gene substitution, which is described below.

The third method for increasing expression of the purine operon includes decreasing expression amount of the purine operon repressor (U.S. Pat. No. 6,284,495).

Expression amount of the purine operon repressor (purine repressor) can be decreased by, for example, a method of treating a *Bacillus* bacterium with ultraviolet ray irradiation or a mutagen used in a usual mutagenesis treatment such as NTG or EMS and selecting a mutant showing decreased expression of the purine repressor.

Furthermore, a *Bacillus* bacterium with decreased expression of the purine repressor can also be obtained by, for example, besides a mutagenesis treatment, replacing a gene encoding the purine repressor on a chromosome (purR, GenBank Accession NC_000964) with a corresponding gene that does not normally function (hereafter, also referred to as "disrupted-type gene") by homologous recombination utilizing a gene recombination technique (Experiments in Molecular Genetics, Cold Spring Harbor Laboratory Press (1972); Matsuyama, S. and Mizushima, S., J. Bacteriol., 1985, 162, 1196-1202).

Furthermore, an ability to produce a purine-derived substance can also be enhanced by attenuating uptake of purine-derived substances into cells. For example, the uptake of purine nucleosides by the cells can be attenuated by blocking a reaction involved in the uptake of purine nucleosides by the cells. Examples of the reaction involved in the uptake of purine nucleosides by the cells include reactions catalyzed by nucleoside permeases.

Furthermore, when a purine nucleoside is produced, activity of an enzyme which decomposes purine-derived substances may be decreased in order to enhance the ability to produce the purine nucleoside. Examples of such an enzyme include purine nucleoside phosphorylase.

Purine nucleotides biosynthesized from PRPP by enzymes involved in purine biosynthesis are dephosphorylated and thereby converted into a purine nucleoside. To efficiently cause accumulation of a purine nucleoside, it is preferable to reduce activities of purine nucleoside phosphorylases, which further degrade purine nucleosides into hypoxanthine or the like. That is, it is preferable to attenuate or eliminate activity of a purine nucleoside phosphorylase that employs purine nucleosides such as inosine as a substrate.

Specifically, the purine nucleoside phosphorylase activity can be decreased by disrupting the deoD and pupG genes encoding purine nucleoside phosphorylase in *Bacillus* bacteria. The *Bacillus* bacterium used in the present invention may be modified by disrupting one or both of the deoD and pupG genes. As the deoD and pupG genes, for example, those genes derived from *Bacillus* bacteria (deoD; Genbank Accession No. NC_000964, pupG; Genbank Accession No. NC_000964) can be used.

The ability to produce a purine-derived substance may also be enhanced by decreasing the activity of succinyl-AMP synthase. Examples of the gene encoding succinyl-AMP synthase include the purA gene. Examples of the purA gene include, for example, those having the nucleotide sequence registered as GenBank Accession No. NC_000964 (coding region corresponds to the nucleotide numbers 4153460 to 4155749 of the complementary strand).

The ability to produce a purine-derived substance may also be enhanced by decreasing activity of inosine monophosphate (IMP) dehydrogenase. Examples of the gene encoding IMP dehydrogenase include the guaB gene. Examples of the guaB gene include, for example, those having the nucleotide sequence registered as GenBank Accession No. NC_000964 (coding region corresponds to the nucleotide numbers 15913 to 17376).

Moreover, as a method for enhancing an ability to produce purine-derived substance, amplification of a gene encoding a protein having an activity of excreting a purine-derived substance may be contemplated. An example of a bacterium in which such a gene has been amplified is a *Bacillus* bacterium in which the rhtA gene is amplified (Japanese Patent Application Laid-open No. 2003-219876).

More specific examples of the microorganism usable for the present invention include, for example, *Escherichia coli* AJ11442 (NRRL B-12185, FERM BP-1543, refer to U.S. Pat. No. 4,346,170), *Brevibacterium lactofermentum* AJ3990 (ATCC 31269, refer to U.S. Pat. No. 4,066,501) etc. for L-lysine as the target substance, *Escherichia coli* VKPM B-3996 (RIA1867, VKPM B-3996, refer to U.S. Pat. No. 5,175,107), *Corynebacterium acetoacidophilum* AJ12318 (FERM BP-1172) (refer to U.S. Pat. No. 5,188,949) etc. for L-threonine, *Escherichia coli* AJ12604 (FERM BP-3579, refer to European Patent Publication No. 488,424 A), *Brevibacterium lactofermentum* AJ12637 (FERM BP-4160, refer to French Patent Application Laid-open No. 2,686,898) etc. for L-phenylalanine, *Escherichia coli* AJ12624 (FERM BP-3853, refer to French Patent Application Laid-open No. 2,680,178), *Brevibacterium lactofermentum* AJ12475 (FERM BP-2922, refer to U.S. Pat. No. 5,272,067) etc. for L-glutamic acid, *Escherichia coli* AJ11478 (FERM P-5274, refer to Japanese Patent Publication No. 62-34397), *Brevibacterium lactofermentum* AJ3718 (FERM P-2516, refer to U.S. Pat. No. 3,970,519) etc. for L-leucine, *Escherichia coli* KX141 (VKPM B-4781, refer to European Patent Publication No. 519,113 A), *Brevibacterium flavum* AJ12149 (FERM BP-759, refer to U.S. Pat. No. 4,656,135) etc. for L-isoleucine, *Escherichia coli* VL1970 (VKPM B-4411, refer to the European Patent Publication No. 519,113 A), *Brevibacterium lactofermentum* AJ12341 (FERM BP-1763, refer to U.S. Pat. No. 5,188,948) etc. for L-valine, and *Corynebacterium glutamicum* AJ12092 (FERM BP-6906) for L-arginine.

Production of a target substance using the present invention can be attained by controlling concentration of ammonia to be within a certain concentration range for at least a preferred period, that is, at least part of the whole culture process during fermentation.

The preferred period within the whole culture process during fermentation means a period in which the culture is performed with the ammonia concentration being controlled at a certain concentration. It is preferred to control during the period the production of the substance is performed. For example, when the method of the present invention includes a stage for proliferating a microorganism having an ability to produce the substance (proliferation phase) and a stage for producing the substance (substance production phase), the ammonia concentration may be controlled at a certain concentration in the substance production phase, and the ammonia concentration may be or may not be controlled at a certain concentration in the proliferation phase for proliferating the microorganism.

The "proliferation phase" means the stage when the carbon source is primarily used for cell growth, that is, the stage when the microorganism is logarithmically proliferating, which may be a period within 3 hours, preferably 6 hours, more preferably 10 hours from the start of the culture. The "substance production phase" means the stage when the carbon source is mainly used for substance production, which may a period after 3 hours, preferably 6 hours, more preferably 10 hours from the start of the culture.

The certain concentration range can be used for both the method of performing the culture with controlling ammonia concentration to be within a certain range, and the method of performing the culture with controlling ammonia concentration to be not higher than a certain concentration.

The present invention may be applied to a method of culturing in which bicarbonate ions and/or carbonate ions serve counter ions of amino acids (hereinafter, it may be described as carbonate fermentation). When a basic amino acid such as L-lysine is produced, the production may be performed by a method in which fermentation is performed by controlling the pressure in the fermentation tank to be positive during the fermentation, or by supplying carbon dioxide gas or a mixed gas containing carbon dioxide gas to the medium to provide a culture period where the medium contains 20 mM or more of bicarbonate ions and/or carbonate ions, so that these bicarbonate ions and/or carbonate ions serve as counter ions of cations mainly comprising the basic amino acid, and the objective basic amino acid is then collected (Japanese Patent Application Laid-open No. 2002-65287, U.S. Patent Published Application No. 2002/0025564, EP 1813677 A).

The preferred period within the whole culture process during fermentation in the method of culturing in which bicarbonate ions and/or carbonate ions serve as counter ions of a basic amino acid and collecting the target basic amino acid, is not particularly limited provided that desired productivity is achieved, but specifically, for example, may be not less than one tenth, preferably not less than one fifth of the whole culture process during the main fermentation. More specifically, it may include a period in which pH of the medium increases due to the shortage of counter ions such as sulfate and chloride ions used in the medium while the target basic substance accumulates.

In the carbonate fermentation, pressure in the fermentation tank may be controlled to be positive during the fermentation, and/or carbon dioxide gas or a mixed gas containing carbon dioxide gas may be supplied to the medium. Both the above operations are preferably performed so that there is a culture period where preferably 20 mM or more, more preferably 30 mM or more, particularly preferably 40 mM or more, of bicarbonate ions and/or carbonate ions are present in the medium. The internal pressure of the fermentation tank, supply amount of carbon dioxide gas or mixed gas containing carbon dioxide gas, or the limited gas supply volume can be determined by, for example, measuring bicarbonate ions or carbonate ions in the medium, or the pH or ammonia concentration of the medium.

According to the carbonate fermentation, it is possible to suppress the pH of the medium so that the amount of bicarbonate ions and/or carbonate ions present in the medium as counter ions is smaller than that used in the conventional methods. When the pH is controlled with ammonia, ammonia is supplied in order to increase the pH, and it can serve as a nitrogen source for the basic amino acid. Examples of cations other than the basic amino acid in the medium include K, Na, Mg, Ca etc. originating in medium components. These preferably exist in an amount of 10% or less, preferably 5% or less, more preferably 2% or less of the total cations.

Furthermore, the internal pressure of the fermentation tank during fermentation can be made positive by, for example, making the gas supply pressure higher than the exhaust pressure. By making the internal pressure of the fermentation tank positive, the carbon dioxide gas generated by fermentation dissolves in the culture medium to generate bicarbonate ions or carbonate ions, and these can serve as counter ions of the basic amino acid. The internal pressure of the fermentation tank is, specifically, 0.03 to 0.2 MPa, preferably 0.05 to 0.15 MPa, more preferably 0.1 to 0.3 MPa, in terms of the gage pressure (pressure difference with respect to the atmospheric pressure). Moreover, by supplying carbon dioxide gas or a mixed gas containing carbon dioxide gas to the culture medium, carbon dioxide gas may be dissolved in the medium. Furthermore, when supplying carbon dioxide gas or a mixed gas containing carbon dioxide to the medium, the internal pressure of the fermentation tank may be adjusted to be positive.

The internal pressure of the fermentation tank may be adjusted to be positive by, for example, making the gas supply pressure higher than the exhaust pressure. Specifically, it is preferred to culture by adjusting the partial pressure of oxygen higher than that of carbon dioxide. Furthermore, when carbon dioxide gas is supplied to the medium, for example, pure carbon dioxide or a mixed gas containing 5 volume % or more of carbon dioxide may be bubbled into the medium.

The aforementioned methods for dissolving bicarbonate ions and/or carbonate ions in the medium may be used independently, or two or more of them may be used in combination.

In the conventional methods, a sufficient amount of ammonium sulfate or ammonium chloride is usually added to the medium to serve as counter anions of the basic amino acid to be produced, and sulfuric acid or hydrochloric acid decomposition products of proteins etc. are also added to the medium as a nutrient component. Therefore, the sulfate ions and chloride ions generated from them are present in the medium. Therefore, the concentration of the weakly acidic carbonate ions is extremely low during the culture, such as a ppm order. The above embodiment of the present invention is characterized in that these sulfate ions and chloride ions are reduced, and the carbon dioxide gas released by the microorganism during fermentation is dissolved in the medium in the aforementioned fermentation environment and used as counter ions. Therefore, in the above embodiment of the present invention, it is not required to add sulfate ions or chloride ions to the medium in an amount more than the amount required for the growth. It is preferred that an appropriate amount of ammonium sulfate or the like is added to the medium at an early stage of the culture, and the addition is terminated in the middle of the culture. Alternatively, ammonium sulfate or the like may be added while maintaining the balance with the dissolved carbonate ions or bicarbonate ions in the medium. Moreover, as a nitrogen source of the basic amino acid, ammonia may be added to the medium. Ammonia may be supplied to the medium independently, or together with other gases.

Lower concentrations of anions other than bicarbonate ions and/or carbonate ions in the medium are more preferred so long as they are present in amounts that are required for the growth of the microorganism. Examples of such anions include chloride ions, sulfate ions, phosphate ions, ionized organic acids, hydroxide ions, and so forth. The total molar concentration of these other ions is usually preferably 900 mM or lower, more preferably 700 mM or lower, still more preferably 500 mM or lower, further preferably 300 mM or lower, particularly preferably 200 mM or lower.

To reduce the amounts of sulfate ions and/or chloride ions to be used is one of the objects of the above embodiment of the present invention, and the total amount of sulfate ions or chloride ions, or both contained in the medium is usually 700 mM or lower, preferably 500 mM or lower, more preferably 300 mM or lower, still more preferably 200 mM or lower, particularly preferably 100 mM or lower.

If ammonium sulfate is added to a medium as a counter ion source of a basic amino acid, carbon dioxide gas in the culture medium is usually eliminated by sulfate ions. However, in the above embodiment of the present invention, it is not necessary to add an excess amount of ammonium sulfate to the medium, and therefore carbon dioxide gas can be easily dissolved in the fermentation medium.

Furthermore, in the above embodiment of the present invention, it is preferable to control the total ammonia concentration in the medium to such an extent that "production of the basic amino acid is not inhibited". Examples of the conditions to attain such a purpose include, for example, those for providing yield and/or productivity of preferably 50% or more, more preferably 70% or more, particularly preferably 90% or more, of the yield and/or productivity obtained under optimal conditions. Specifically, the total ammonia concentration in the medium is, for example, 300 mM or lower, 250 mM or lower, 200 mM or lower, 100 mM or lower, or 50 mM or lower. The dissociation degree of the ammonia decreases as the pH becomes higher. Non-ionized ammonia is more toxic to bacteria than ammonium ions. Therefore, the upper limit of the total ammonia concentration should be determined depending on the pH of the culture medium. That is, as the pH of the culture medium increases, the acceptable total ammonia concentration decreases. Therefore, the aforementioned total ammonia concentration "which does not inhibit the basic amino acid production" is preferably determined for each specific pH value. However, the total ammonia concentration range that is acceptable at the highest pH level during the culture may be used as the upper limit of the total ammonia concentration throughout the entire culture period.

On the other hand, the total ammonia concentration which functions as a source of nitrogen for growth of the microorganism and production of the basic substance is not particularly limited, and can be appropriately determined, so long as a reduced level of the nitrogen source which can result in continuous depletion of ammonia during the culture does not reduce productivity of the objective substance by the microorganism. For example, the ammonia concentration can be measured over time during the culture, and if ammonia in the medium is depleted, a small amount of ammonia may be added to the medium. Although the total ammonia concentration after the addition of ammonia is not particularly limited, the total ammonia concentration may be, for example, preferably 1 mM or higher, more preferably 10 mM or higher, particularly preferably 20 mM or higher.

Furthermore, in L-glutamic acid fermentation, the culture can be performed with precipitating L-glutamic acid in the medium by using a liquid medium adjusted to have a condition under which L-glutamic acid is precipitated. The condition under which L-glutamic acid is precipitated is, for example, pH 5.0 to 4.0, preferably pH 4.5 to 4.0, more preferably pH 4.3 to 4.0, particularly preferably pH 4.0 (European Patent Publication No. 1078989 A).

EXAMPLE

Production of L-Arginine Using the Apparatus of the Present Invention

This example shows an example of application of the ammonia control culture using the apparatus of the present invention to production of L-arginine by a coryneform bacterium. As an L-arginine-producing strain, *Corynebacterium glutamicum* AJ12092 (FERM BP-6906) was used.

The apparatus of the present invention used in this example had the configuration described below.

Ammonia Sensor 10:

Ammonia sensor 10 comprises an internal electrode type sensor using an ammonia permeable membrane, and shows voltage change in response to concentration change of non-ionized ammonia. It was inserted in the culture tank 200.

Ammonia-Controlling Apparatus 100:

There was used a computer having the storage part 106, control part 103, signal input part 108 connected with the ammonia sensor 10, and control output part 104 connected to the ammonia feeder 300. The storage part 106 stores a calibration curve representing relation between the non-ionized ammonia concentration of the culture medium contained in the culture tank 200, and the voltage measured with the ammonia sensor 10. The control part 102 performs the ammonia concentration calculation step of measuring the voltage with the ammonia sensor 10, and calculating the non-ionized ammonia concentration of the culture medium contained in the culture tank 200 from the voltage by using the calibration curve, and the ammonia supply direction step of, when the calculated non-ionized ammonia concentration is lower than a set control concentration, directing the ammonia feeder 300 to supply ammonia to the culture tank 200.

Ammonia Feeder 300:

Ammonia feeder 300 has a container containing an aqueous ammonium sulfate solution, and it is disposed so that the aqueous ammonium sulfate solution can be dropped from the container to the culture tank with a roller pump, and drops the solution at a set dropping rate on the basis of a signal sent from the ammonia-controlling apparatus 100.

Figure 7:
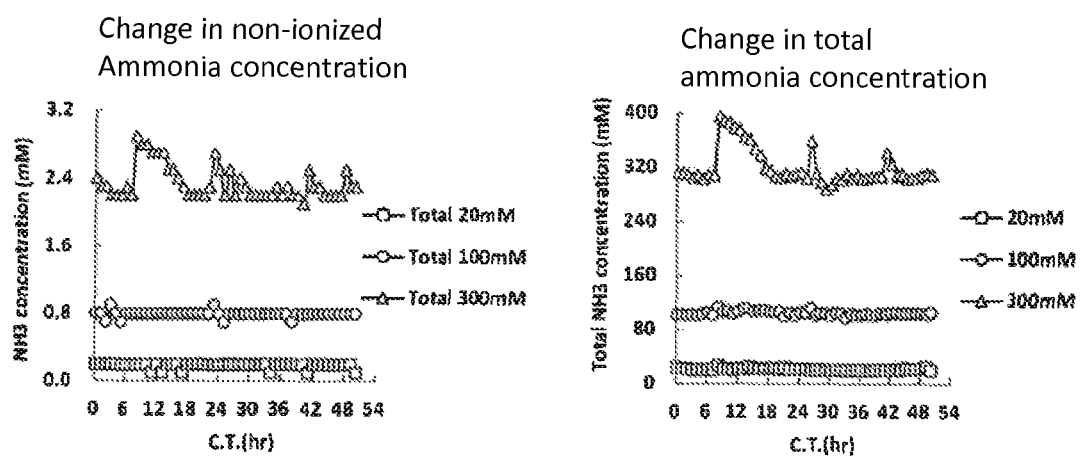
FIG. 7 shows results of control of ammonia concentration obtained in arginine (Arg) production performed by using the apparatus of the example.

(1) Control of Ammonia Concentration in Arg Fermentation Using the Apparatus of the Present Invention L-Arginine was produced with controlling the total ammonia concentration, which essentially decreases with advance of the culture without any control, to be constant by using the apparatus of the present invention. In this production, three kinds conditions of 20 mM, 100 mM, and 300 mM were set as a concentration at which the total ammonia concentration in the medium is to be controlled. 1 N KOH was dropped to 300 mL of the L-arginine production medium shown in Table 1 contained in a jar fermenter to adjust pH of the medium to be 6.9. Ammonium sulfate was mixed in the L-arginine production medium so that the initial total ammonia concentration became 20 mM, 100 mM, or 300 mM. The *Corynebacterium glutamicum* AJ12092 strain was applied to the whole surface of a plate of the CM-Dex agar medium shown in Table 2, and cultured at 31.5° C. for 24 hours, and the cells grown on the agar medium of one plate were inoculated into the medium contained in the jar fermenter. The culture was performed at a stirring rate of 700 rpm with maintaining the temperature to be 31.5° C. and with aeration of 300 mL/minute of air disinfected with a filter. pH of the medium, which essentially decreases with advance of the culture, was maintained to be 6.9 by adding 6 N KOH. Further, a separately sterilized 692 g/L solution of glucose (containing 0.05 mL/L of antifoam GD-113) was appropriately added so that the glucose concentration in the medium, which essentially decreases with advance of the culture, was maintained to be about 40 g/L. The culture was performed for 52 hours. When the non-ionized ammonia concentration became lower than the set value, the aqueous ammonium sulfate solution was automatically dropped by the apparatus of the present invention so that the set total ammonia concentration should be maintained, and the total ammonia concentration was thereby controlled to be constant during the culture. Specifically, the non-ionized ammonia concentration in the medium was measured in real time with the ammonia sensor inserted into the jar fermenter, and a separately sterilized 450 g/L aqueous ammonium sulfate solution was automatically dropped to the medium from the ammonia feeder so that the target total ammonia concentration was maintained. As a result, the Arg fermentation could be performed with automatically maintaining the target non-ionized ammonia concentration and total ammonia concentration as shown in FIG. 7 by using the apparatus of the present invention. For controlling the total ammonia concentration to be 20 mM, 100 mM, and 300 mM, the 450 g/L aqueous ammonium sulfate solution was dropped at rates of 0.77 mL/hr, 0.90 mL/hr, and 1.30 mL/hr (average rates over the whole culture period), respectively. When the total ammonia concentration was controlled to be 300 mM, proofing using an external ammonia sensor was performed by using a sample collected in the middle of the culture (8 hours) and sufficiently made alkaline for converting contained ammonium ion to non-ionized ammonia.

By the results of this experiment, it was demonstrated that, in the production of L-amino acid by fermentation, culture can be performed with automatically controlling the ammonia concentration in the medium (non-ionized ammonia concentration and total ammonia concentration) to be constant by using the apparatus of the present invention.

Figure 8:
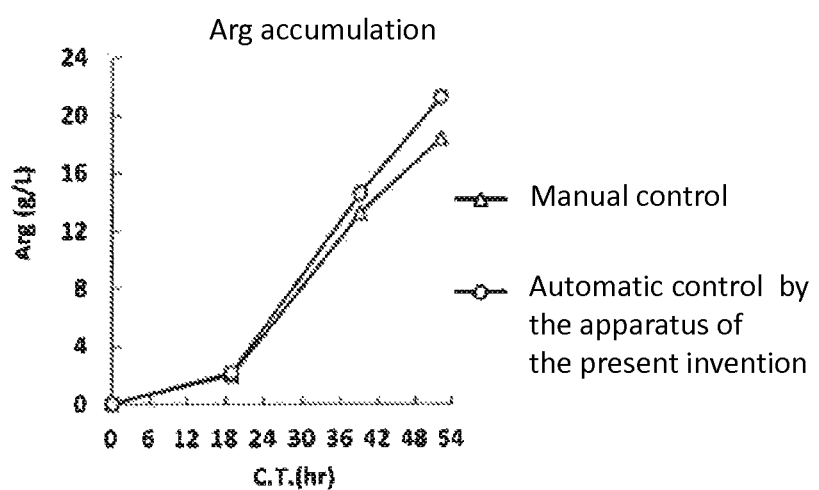
FIG. 8 shows accumulation of Arg observed in the Arg production performed by using the apparatus of the example.
Figure 9:
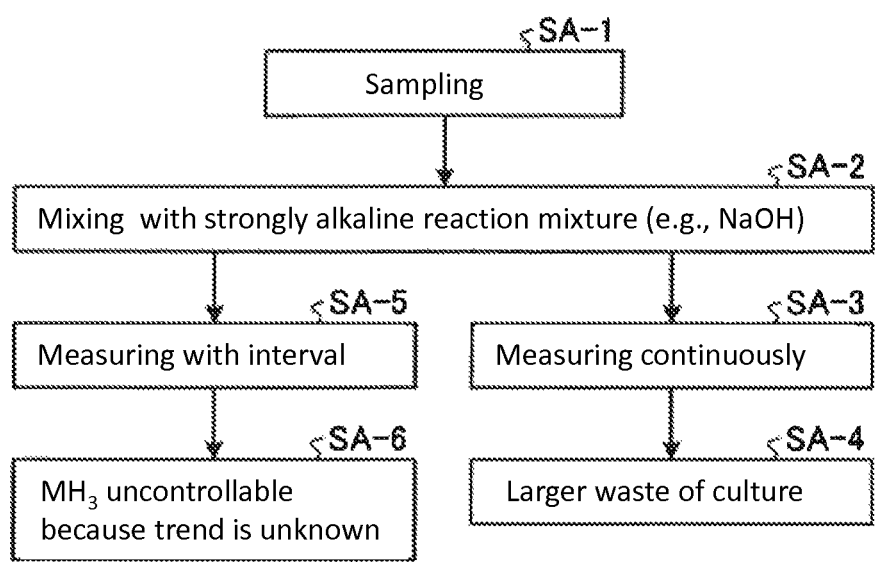
FIG. 9 is a flowchart showing an example of the process of conventional ammonia concentration control.

(2) Improvement in Arg Productivity Provided by Use of the Apparatus of the Present Invention Then, Arg production amount obtained by controlling the total ammonia concentration using the apparatus of the present invention and the same obtained by controlling the total ammonia concentration using a common manual control method were compared. The total ammonia concentration to which the concentration in the medium was to be controlled was set to be 300 mM. 1 N KOH was dropped to 300 mL of the L-arginine production medium shown in Table 1 contained in a jar fermenter to adjust pH of the medium to be 6.9. Ammonium sulfate was mixed in the L-arginine production medium so that the initial ammonia concentration became 300 mM. The *Corynebacterium glutamicum* AJ12092 strain was applied to the whole surface of a plate of the CM-Dex agar medium shown in Table 2, and cultured at 31.5° C. for 24 hours, and the cells grown on the agar medium of one plate were inoculated into the medium contained in the jar fermenter. The culture was performed at a stirring rate of 700 rpm with maintaining the temperature to be 31.5° C. and with aeration of 300 mL/minute of air disinfected with a filter. pH of the medium, which essentially decreases with advance of the culture, was maintained to be 6.9 by adding 6 N KOH. Further, a separately sterilized 692 g/L solution of glucose (containing 0.05 mL/L of antifoam GD-113) was appropriately added so that the glucose concentration in the medium, which essentially decreases with advance of the culture, was maintained to be about 40 g/L. The culture was performed for 52 hours. The total ammonia concentration was controlled by two kinds of methods, i.e., the method of using the apparatus of the present invention like the experiment described in the previous section, and a method of manually adding 3 mL of the 450 g/L aqueous ammonium sulfate solution when the total ammonia concentration became lower than the set value (control value). As a result, when the apparatus of the present invention was used, the total ammonia concentration could be automatically controlled. On the other hand, when the total ammonia concentration was manually controlled, the ammonium sulfate aqueous solution must be manually added 17 times during the culture of 52 hours. Further, as shown in FIG. 8, when the apparatus of the present invention was used, arginine accumulated at a higher concentration compared with the case where the total ammonia concentration was manually controlled. Furthermore, as for the total arginine production amount, 11.1 g of arginine was produced in the case of using the apparatus of the present invention, whereas 9.5 g of arginine was produced in the case of the manual control.

In this experiment, proofing using an external ammonia sensor was performed by using a culture medium collected in the middle of the culture (8 hours) and sufficiently made alkaline for converting contained ammonium ion to non-ionized ammonia.

By the results of this experiment, it was demonstrated that, in the production of L-amino acid by fermentation, culture can be performed with automatically controlling the ammonia concentration in the medium (non-ionized ammonia concentration and total ammonia concentration) to be constant, and in addition, L-amino acid-producing ability can also be improved by using the apparatus of the present invention.

TABLE 1

L-arginine production medium

| | For initial ammonia concentration of 20 mM | For initial ammonia concentration of 100 mM | For initial ammonia concentration of 300 mM |
|---|---|---|---|
| Glucose | 40 g/L | 40 g/L | 40 g/L |
| Soybean protein hydrolysate (6.57 ml/L of hydrolysate containing 35 g of nitrogen/L) | 0.23 g/L (in terms of nitrogen weight) | 0.23 g/L (in terms of nitrogen weight) | 0.23 g/L (in terms of nitrogen weight) |
| $KH_2PO_4$ | 1.00 g/L | 1.00 g/L | 1.00 g/L |
| $(NH_4)_2SO_4$ | 1.32 g/L | 6.6 g/L | 19.8 g/L |

TABLE 1-continued

L-arginine production medium

| | For initial ammonia concentration of 20 mM | For initial ammonia concentration of 100 mM | For initial ammonia concentration of 300 mM |
|---|---|---|---|
| $MgSO_4 \cdot 7H_2O$ | 0.40 g/L | 0.40 g/L | 0.40 g/L |
| $FeSO_4 \cdot 7H_2O$ | 10 mg/L | 10 mg/L | 10 mg/L |
| $MnSO_4 \cdot 5H_2O$ | 10 mg/L | 10 mg/L | 10 mg/L |
| Thiamin hydrochloride | 0.5 mg/L | 0.5 mg/L | 0.5 mg/L |
| Biotin | 0.5 mg/L | 0.5 mg/L | 0.5 mg/L |
| GD-113 (antifoam) | 0.05 mL/L | 0.05 mL/L | 0.05 mL/L |

The medium was adjusted to pH 6.0 with KOH aqueous solution, and autoclaved at 120° C. for 20 minutes.

TABLE 2

CM-Dex agar medium

| Glucose | 5.0 g/L |
|---|---|
| Polypeptone | 10.0 g/L |
| Yeast extract | 10.0 g/L |
| $KH_2PO_4$ | 1.0 g/L |
| $MgSO_4 \cdot 7H_2O$ | 0.4 g/L |
| $FeSO_4 \cdot 7H_2O$ | 10.0 mg/L |
| $MnSO_4 \cdot 5H_2O$ | 10.0 mg/L |
| Urea | 3.0 g/L |
| Soybean protein hydrolysate (34.3 ml/L of hydrolysate containing 35 g of nitrogen/L) | 1.2 g/L (in terms of nitrogen weight) |
| Biotin | 10.0 µg/L |
| Agar | 20.0 g/L |

The medium was adjusted to pH 7.5 with KOH aqueous solution, and autoclaved at 120° C. for 20 minutes. After the autoclaving, the medium was poured into a petri dish and gelled.

By the results of the experiments described above, it was demonstrated that, in the production of L-amino acid by fermentation, culture can be performed with controlling the ammonia concentration in the medium to be constant by using the apparatus of the present invention.

INDUSTRIAL APPLICABILITY

As explained above in detail, according to the present invention, culture can be performed with continuously and arbitrarily controlling the ammonia concentration in the culture medium, and therefore it can be used in the fields of microbial industry, chemical industry, and so forth.

DESCRIPTION OF NUMERICAL NOTATIONS

100 Ammonia-controlling apparatus
102 Control part
102*a* Calibration curve creation part
102*b* Non-ionized ammonia concentration calculation part
102*c* pH value measurement part
102*d* Total ammonia concentration calculation part
102*e* Ammonia supply direction part
102*f* Voltage for proofing measurement part
102*g* Proofing part
104 Control output part
106 Storage part
106*a* Ammonia dissociation curve file
106*b* Calibration curve file 106c Non-ionized ammonia concentration file
106d pH value file
106e Total ammonia concentration file
108 Signal input part
10 Ammonia sensor
11, 13 NH₃ amplifier
12 External ammonia sensor
20 pH Sensor
21 pH Amplifier
200 Culture tank
300 Ammonia feeder
30 Ammonia tank
31 Switch
32 Valve

The invention claimed is:

1. A method for producing a basic amino acid selected from the group consisting of L-lysine, L-arginine, and L-histidine by fermentation comprising culturing a microorganism having an ability to produce the basic amino acid in a culture medium contained in a culture tank to produce and accumulate the basic amino acid in the culture medium, wherein total ammonia concentration of the culture medium is continually adjusted to be within a certain concentration range which is sufficient to enhance production of the basic amino acid during at least a part of the total culture process by using an ammonia-controlling apparatus, said ammonia-controlling apparatus comprising at least an ammonia feeder that supplies ammonia to the culture tank, an ammonia sensor, and a control part, wherein:
the ammonia sensor responds to non-ionized ammonia in the culture medium contained in the culture tank,
the control part comprises a processing unit and is connected to the ammonia feeder and the ammonia sensor, and
the control part is configured to
(i) create a calibration curve representing a relation between non-ionized ammonia concentration of the culture medium and a signal from the ammonia sensor,
(ii) calculate non-ionized ammonia concentration of the culture medium from the signal from the ammonia sensor by using the calibration curve, and
(iii) transmit an electric signal to the ammonia feeder when the calculated non-ionized ammonia concentration is lower than a predetermined concentration thereby directing the ammonia feeder to supply ammonia to the culture tank.

2. The method according to claim 1, wherein the certain concentration range is 300 mM or lower.

3. The method according to claim 1, wherein the certain concentration range is 100 mM or lower.

4. The method according to claim 1, wherein the ammonia-controlling apparatus is further connected to a pH sensor for measuring pH value of the culture medium contained in the culture tank, and
wherein the control part further calculates total ammonia concentration from the non-ionized ammonia concentration calculated and the pH value measured with the pH sensor on the basis of an ammonia dissociation curve representing an existing ratio of non-ionized ammonia and ammonium ion in the culture medium at each pH value, and
the total ammonia concentration is used instead of the non-ionized ammonia concentration.

5. The method according to claim 4, wherein the control part further proofs the calibration curve so that the non-ionized ammonia concentration calculated from a signal for proofing on the basis of the calibration curve corresponds to the total ammonia concentration calculated by the total ammonia concentration calculation means, and
the signal for proofing is obtained by:
collecting a culture medium from the culture tank,
making the culture medium sufficiently alkaline to convert ammonium ion into non-ionized ammonia, and
measuring non-ionized ammonia concentration of the culture medium with an external ammonia sensor outside the culture tank.

6. The method according to claim 5, wherein the ammonia-controlling apparatus is connected to the external ammonia sensor, and
wherein the control part further inputs the signal from the external ammonia sensor, as the signal for proofing.

7. The method according to claim 1, wherein the ammonia-controlling apparatus is configured to keep the total ammonia concentration in a predetermined range.

8. The method according to claim 1, wherein the ammonia-controlling apparatus further comprises a user interface.

9. The method according to claim 1, wherein the ammonia-controlling apparatus is configured for real-time controlling of ammonia in a culture medium.

10. The method according to claim 1, wherein the ammonia-controlling apparatus is configured for controlling ammonia in a culture medium of more than one culture tank.

11. The method according to claim 1, wherein the ammonia-controlling apparatus is configured for controlling ammonia in the culture medium at intervals of 5 minutes or less.

12. The method according to claim 5, wherein the ammonia-controlling apparatus is configured for proofing the calibration curve at intervals of 12 hours or less.

13. The method according to claim 1, wherein the ammonia-controlling apparatus is configured for controlling ammonia for at least a part of the culture period or the entire culture period.

* * * * *